US005767268A

United States Patent [19]
Chucholowski et al.

[11] Patent Number: 5,767,268
[45] Date of Patent: Jun. 16, 1998

[54] SULFURIC ACID ESTERS OF AMINO SUGARS

[75] Inventors: Alexander Chucholowski, Grenzach-Wyhlen; Jürgen Fingerle, Rheinfelden, both of Germany; Niggi Iberg, Basel, Switzerland; Hans Peter Märki, Basel, Switzerland; Rita Müller, Basel, Switzerland; Michael Pech, Hartheim, Germany; Marianne Rouge, Basel, Switzerland; Gerard Schmid, Kienberg, Switzerland; Thomas Tschopp, Ettingen, Switzerland; Hans Peter Wessel, Heitersheim, Germany

[73] Assignee: Hoffmann-La Roche Inc., Nutley, N.J.

[21] Appl. No.: 639,985

[22] Filed: Apr. 26, 1996

[30] Foreign Application Priority Data

May 5, 1995 [CH] Switzerland ............... 01 311/95

[51] Int. Cl.$^6$ ............... C07H 5/04; C07H 15/00; A61K 31/70
[52] U.S. Cl. ............... 536/29.1; 536/4.1; 536/17.5; 536/17.6; 536/17.9; 514/23; 514/27; 514/42; 564/342
[58] Field of Search ............... 536/4.1, 17.5, 536/17.6, 17.9, 29.1; 514/23, 25, 27, 42; 564/342

[56] References Cited

U.S. PATENT DOCUMENTS

| | | | |
|---|---|---|---|
| 4,120,954 | 10/1978 | Joseph et al. | 514/25 |
| 4,431,637 | 2/1984 | Upeslacis et al. | 514/25 |
| 5,008,247 | 4/1991 | Meinetsberger | 514/23 |
| 5,037,973 | 8/1991 | Meinetsberger | 536/53 |
| 5,298,616 | 3/1994 | Hosang et al. | 536/118 |
| 5,447,919 | 9/1995 | Hosang et al. | 514/53 |
| 5,521,160 | 5/1996 | Chucholowski et al. | 514/42 |
| 5,565,432 | 10/1996 | Novak et al. | 514/25 |

FOREIGN PATENT DOCUMENTS

| | | |
|---|---|---|
| 312086 | 10/1988 | European Pat. Off. |
| 1230031 | 12/1966 | Germany |

OTHER PUBLICATIONS

Collins & Ferrier, Monosaccharides: Their Chemistry and Their Roles in Natural Products, John Wiley & Sons, p. 4, 1995.

Teien et al., *Thrombosis Research*, 10: pp. 399–410 (1977).
Meyer zu Reckendorf, *Chem. Ber.*, 107: pp. 870–874 (1974).
Heyns & Paulsen, *Chem. Ber.*, 88: pp. 188–195 (1955).
Weidmann, *Liebigs Ann. Chem.*, 679: 178–86, (1964).
Osman et al., *J. Am. Chem. Soc.*, 73: pp. 2726–2729 (1951).
Wyss & Kiss, *Helv. Chim. Acta*, 58: pp. 1833–1847 (1975).
Stempel et al., *J. Am. Chem. Soc.*, 73: pp. 455–456 (1951).
Wessel et al., *Bioorg. Chem. Lett.*, 4: pp. 1419–1422 (1994).

Primary Examiner—John Kight
Assistant Examiner—Howard C. Lee
Attorney, Agent, or Firm—George W. Johnston; William H. Epstein; John P. Parise

[57] ABSTRACT

Compounds of formulas $$G^1-N(H)-C(=O)-B-C(=O)-N(H)-G^2 \quad \text{Ia}$$

(Ib: 1,4,5,8-naphthalenetetracarboxylic diimide with $G^1-N$ and $N-G^2$ substituents)

or (Ic: 5-($G^3$-NH-C(=O)-)-1,3-benzenedicarboxamide with $G^1-NH-C(=O)-$ and $-C(=O)-NH-G^2$)

wherein,

B is lower alkylene or an optionally substituted aromatic ring system;

$G^1$, $G^2$ and $G^3$ each independently signify a residue of a glycopyranoside, a glycopyranose or a derivative thereof, with at least one hydroxy group of residue $G^1$, $G^2$ or $G^3$ being esterified with sulfuric acid, and pharmaceutically usable salts thereof, are useful for the treatment of disorders which are characterized by excessive or destructive proliferation of smooth muscle cells.

19 Claims, 2 Drawing Sheets

SULFURIC ACID ESTERS OF AMINO SUGARS

SUMMARY OF THE INVENTION

The present invention relates to sulfuric acid esters of amino sugars of formula $$\text{G}^1\text{—NH—CO—B—CO—NH—G}^2 \quad \text{Ia}$$

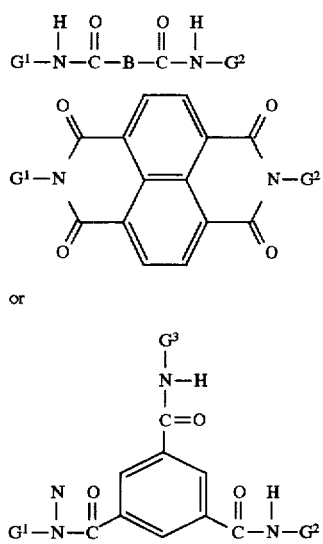

or

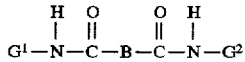

wherein,

B is lower alkylene or an optionally substituted aromatic ring system;

G$^1$, G$^2$ and G$^3$ each independently signify a residue of a glycopyranoside, or glycopyranose or a derivative thereof, wher least one hydroxy group of residue G$^1$, G$^2$ or G$^3$ being esterified with sulfuric acid; and pharmaceutically usable salts thereof.

In another aspect, the invention relates to pharmaceutical preparations containing a compound of formula Ia–Ic or a salt 25 thereof; the use of the compounds of formulas Ia–Ic and their salts as medicaments, especially for the treatment and/or prophylaxis of disorders which are characterized by excessive or destructive proliferation of smooth muscle cells and of arteriosclerotic changes to the vascular wall, for example, for the prevention of restenosis after coronary or peripheral angioplasty or after bypass operations and the like, and, respectively, for the production of medicaments for the said indications; as well as a process for the manufacture of the compounds of formulas Ia–Ic and their salts.

DETAILED DESCRIPTION OF THE INVENTION

Figure 1:
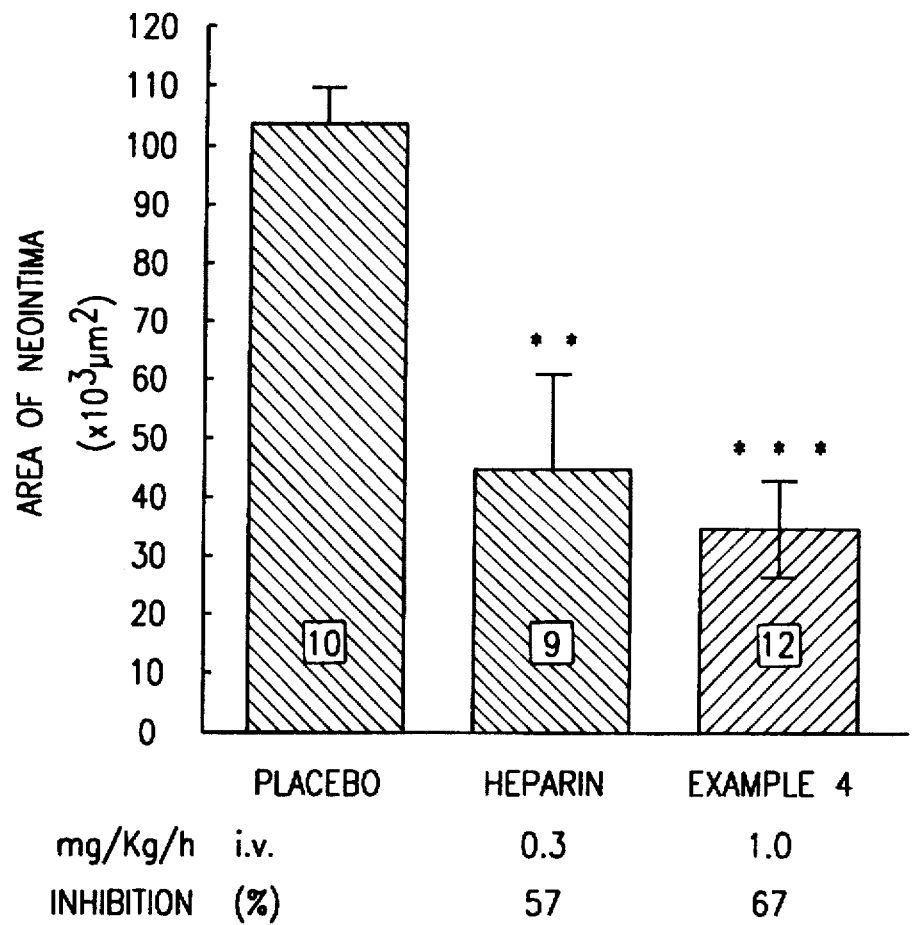
FIGS. 1 and 2 are bar graphs of the cross-sectional area of the neointima in rat carotids of animals administered compounds of the invention compared to animals administered heparin and placebo.

The present invention relates to a compound of formula $$\text{G}^1\text{—NH—CO—B—CO—NH—G}^2 \quad \text{Ia}$$

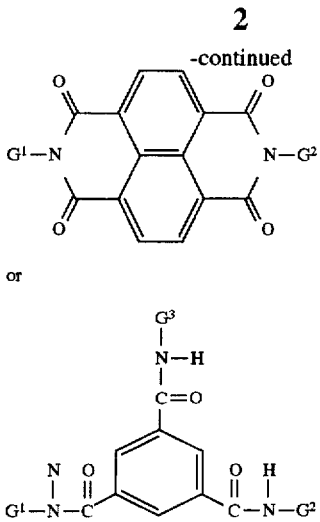

or wherein,

B is lower alkylene, an unsubstituted aromatic ring system or a substituted aromatic system;

G$^1$, G$^2$ and G$^3$ each independently are glycopyranoside, or glycopyranose residues or a derivative thereof, wherein at least one hydroxy group in G$^1$, G$^2$ or G$^3$ is esterified with sulfuric acid; and pharmaceutically usable salts thereof.

In another aspect, the invention relates to pharmaceutical preparations containing a compound of formula Ia–Ic or a salt thereof; the use of the compounds of formulas Ia–Ic and their salts as medicaments, especially for the treatment and/or prophylaxis of disorders which are characterized by excessive or destructive proliferation of smooth muscle cells and of arteriosclerotic changes to the vascular wall, for example, for the prevention of restenosis after coronary or peripheral angioplasty or after bypass operations and the like, and, respectively, for the production of medicaments for the said indications; as well as a process for the manufacture of the compounds of formulas Ia–Ic and their salts.

The compounds of the invention have two or three residues derived from a glycopyranose which are linked with a central element via an amide or imide bridge.

In a preferred embodiment of the invention, G$^1$, G$^2$ and G$^3$ are the same and are selected from the group consisting of

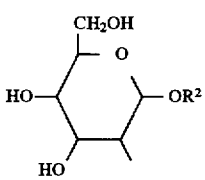

a)

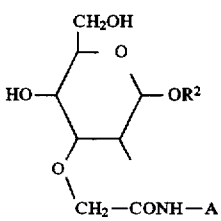

b)

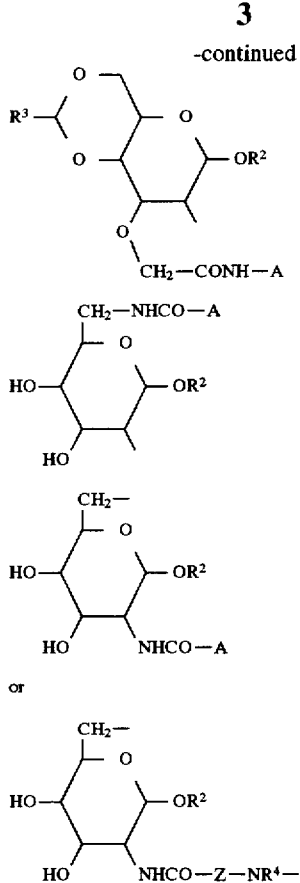

in which in each case at least one hydroxy group of a)–f) is esterified with sulfuric acid and wherein $R^2$ is hydrogen, lower alkyl or benzyl;

$R^3$ is hydrogen, lower alkyl or phenyl;

$R^4$ is hydrogen, unsubstituted lower alkyl or substituted lower alkyl;

Z is unsubstituted phenylene or substituted phenyelene;

A is a sugar alcohol devoid of the 1-hydroxy group or a derivative thereof, tris-(hydroxymethyl)-methyl, glycopyranoside or glycopyranose or a residue of formula g) or h)

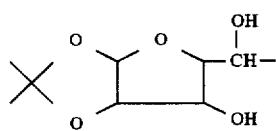

or

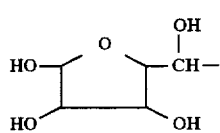

in which in each case at least one hydroxy group in A is esterified with sulfuric acid.

B is phenylene, naphthylene or a group of the formula

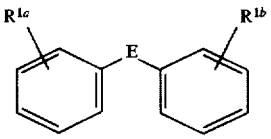

wherein

E is a carbon-carbon bond, —O—, —CO, —CH$_2$—, —CH$_2$CH$_2$—, —CH=CH—or —C≡C—, and $R^{1a}$ and $R^{1b}$ are hydrogen or halogen; and the sugar alcohol is glucitol A galacitol, mannitol, gulitol, arabinitol, ribitol, xylitol, threitol, erythritol or glycerol.

$R^2$ is preferably benzyl.

When $R^4$ is substituted, then the substituent is conveniently an OH group, which can be esterified with sulfuric acid.

Substituents on Z are conveniently the nitro group or the acetylamino group.

Any conventional sugar alcohol can be used. Examples of suitable sugar alcohols from which residue A is derived are hexitols such as glucitol, galactitol, mannitol and gulitol; pentitols such as arabinitol, ribitol and xylitol, tetritols such as threitol and erythritol or glycerol. Derivatives of such sugar alcohols can be mono- or multiply-desoxygenated sugar alcohols.

These sugar alcohols can be present in the D or L form or as racemates, with the naturally occurring form or the form which corresponds to the basic, naturally occurring sugar being preferred.

The terms "lower alkyl" and "lower alkylene" include straight-chain or branched saturated hydrocarbon groups with up to 7, preferably up to 4, carbon atoms such as methyl, ethyl, n-propyl, isopropyl, n-butyl, isobutyl, tert.butyl and the like and, respectively, methylene, ethylene and the like.

The term "halogen" includes fluorine, chlorine, bromine and iodine, of which chlorine is preferred.

Phenylene groups are 1,3- or 1,4-phenylene groups.

Naphthylene groups are 1,4- or 2,6-naphthylene groups.

Examples of salts of compounds of general formulae Ia–Ic are alkali metal salts such as Na or K salts, ammonium salts and salts of tertiary amines such as triethylamine or pyridinium or imidazolium salts or quaternary ammonium salts such as dodecyltrimethylammonium, ethylpyridinium and benzethonium salts; as well as alkaline earth metal salts such as Ca or Mg salts.

Preferred compounds of formulas Ia–Ic are:

(Biphenyl-4,4'-dicarboxylic acid) bis-[[benzyl 3-O-[(benzyl 2-desoxy-2,3,4-tri-O-sulfo-a-D-glucopyranoside)- 2-yl-carbamoylmethyl]-4,6-(R)-O-benzylidene-2-desoxy-a-D-glucopyranosid-2-yl]-amide] hexasodium salt (Example 11).

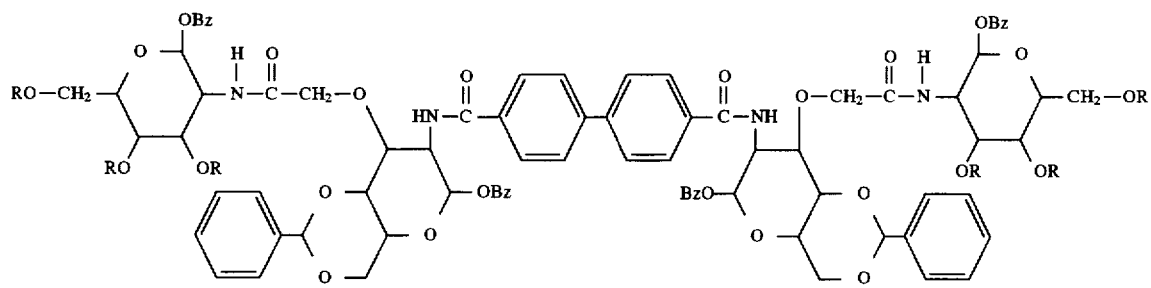

Biphenyl-4,4'-dicarboxylic acid bis-[[benzyl 2,6-didesoxy-3,4-di-O-sulfo-6-(2,3,4,5,6-penta-O-sulfo-D-gluconoylamino)-a-D-glucopyranosid-2-yl]-amide] tetradecasodium salt (Example 14).

-3,4-di-O-sulfo-a-D-glucopyranosid-2-yl]-amide] tetradecasodium salt (Example 23).

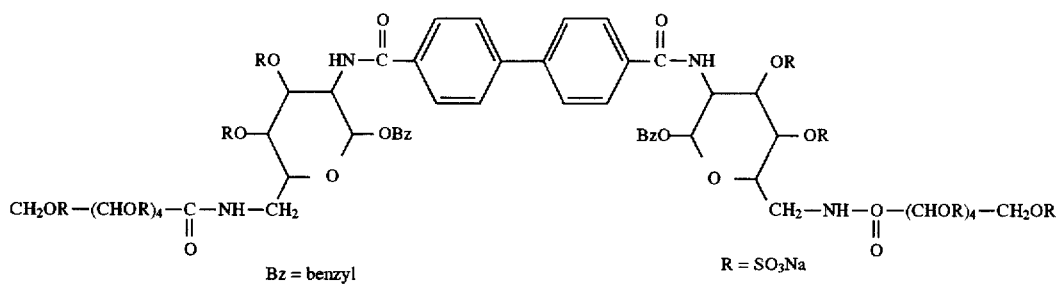

Biphenyl-4,4'-dicarboxylic acid bis-[[(Z)-benzyl 2,6-didesoxy-3,4-di-O-sulfo-6-(3-desoxy-2,4,5,6-tetra-O-sulfo-D-erythro-hex-2-enonoylamino)-a-D-glucopyranosid-2-yl]-amide] dodecasodium salt (Example 15).

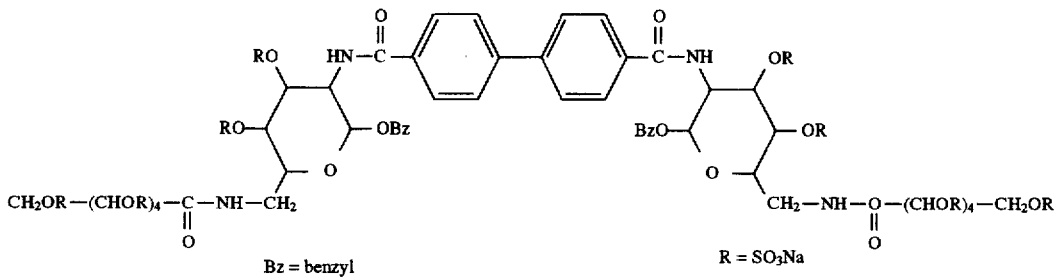

(Z)-Stilbene-4,4'-dicarboxylic acid bis-[[benzyl 2,6-didesoxy-20 6-(2,3,4,5,6-penta-O-sulfo-D-gluconoylamino)

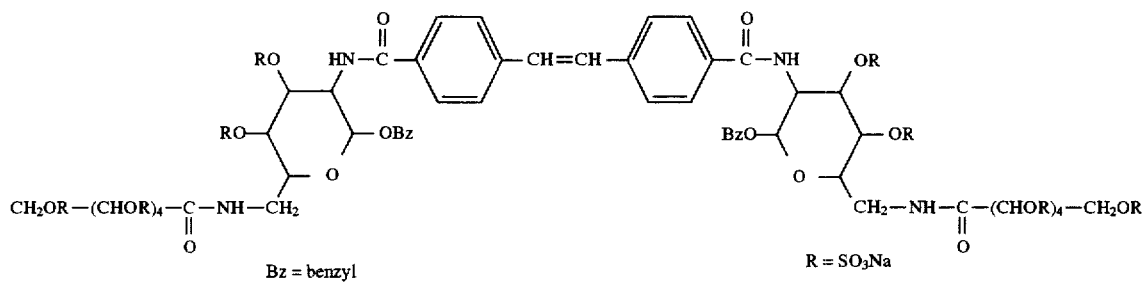

Isophthalic acid bis-[[benzyl 2,6-didesoxy-6-(2,3,4,5,6-penta-O-sulfo-D-gluconoylamino)-3,4-di-O-sulfo-a-D-gluco-pyranosid-2-yl]-amide] tetradecasodium salt (Example 24).

(E)-2-Chloro-stilbene-4,4'-dicarboxylic acid bis-[[benzyl 2,6-didesoxy-2-[4-(2,3,4,5,6-penta-O-sulfo-D-glucit-1-ylamino)- 3-nitro-benzoylamino]-3,4-di-O-sulfo-a-D-glucopyranosid-6-yl]-amide] tetradecasodium salt (Example 32).

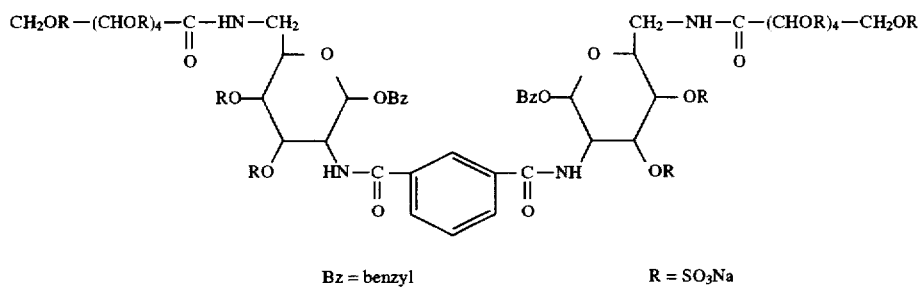

Benzene-1,3,5-tricarboxylic acid tris-[[benzyl 2,6-didesoxy-2-[4-(2,3,4,5,6-penta-O-sulfo-D-glucit-1-ylamino)-3-nitro-benzoylamino]-3,4-di-O-sulfo-a-D-glucopyranosid-6-yl]-amide] henicosasodium salt (Example 30).

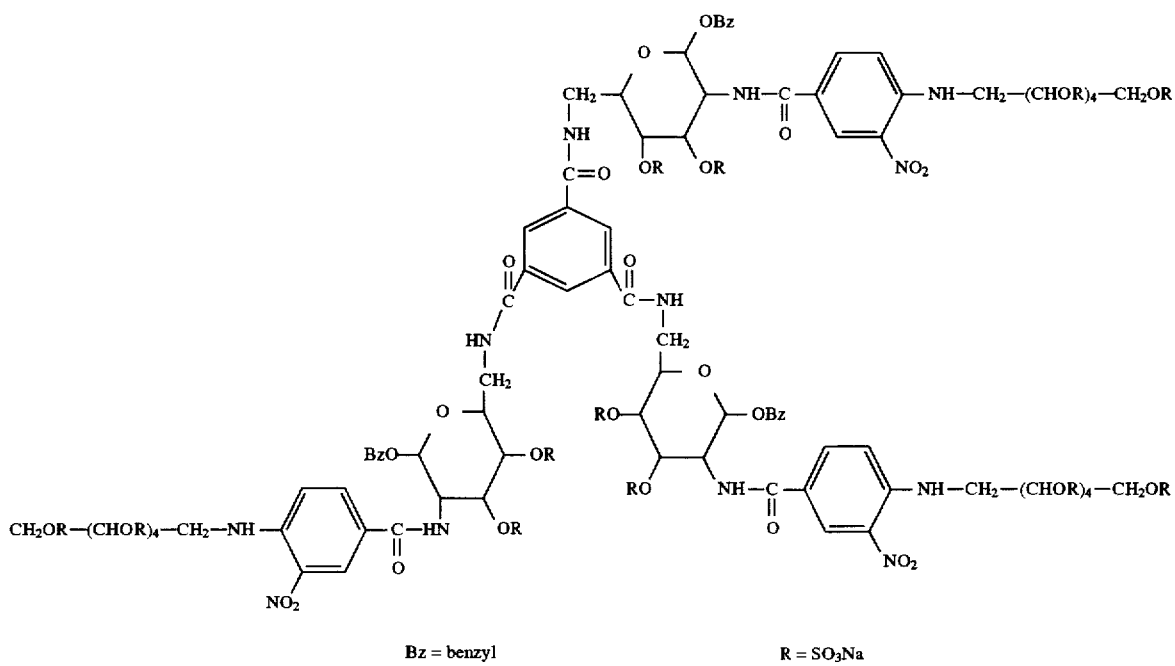

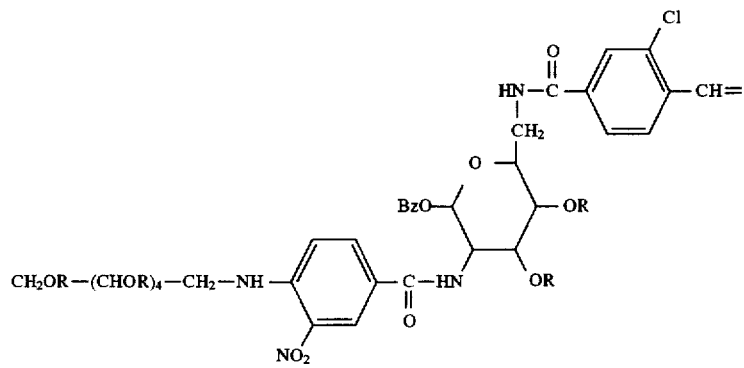

Bz = benzyl

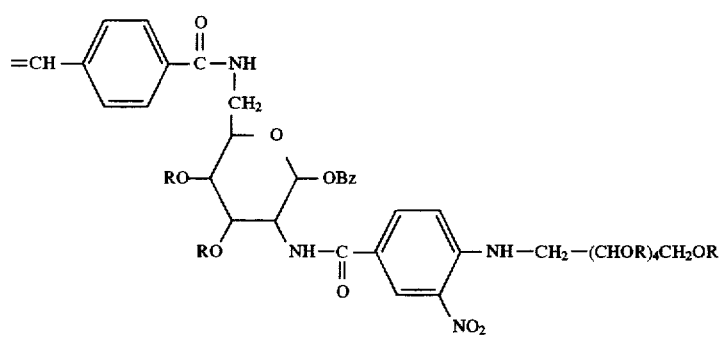

R = SO₃Na

Isophthalic acid bis-[[benzyl 2,6-didesoxy-2-[4-(2,3,4,5,6-penta-O-sulfo-D-glucit-1-ylamino)-3-nitro-benzoylamino]-3,4-di-O-sulfo-a-D-glucopyranosid-6-yl]-amide] tetradecasodium salt (Example 33).

O-sulfo-a-D-1 5 glucopyranosid-6-yl]-1,2,3,6,7,8-hexahydro-benzo[lmn][3,8] phenanthroline-1,3,6,8-tetraone tetradecasodium salt (Example 34).

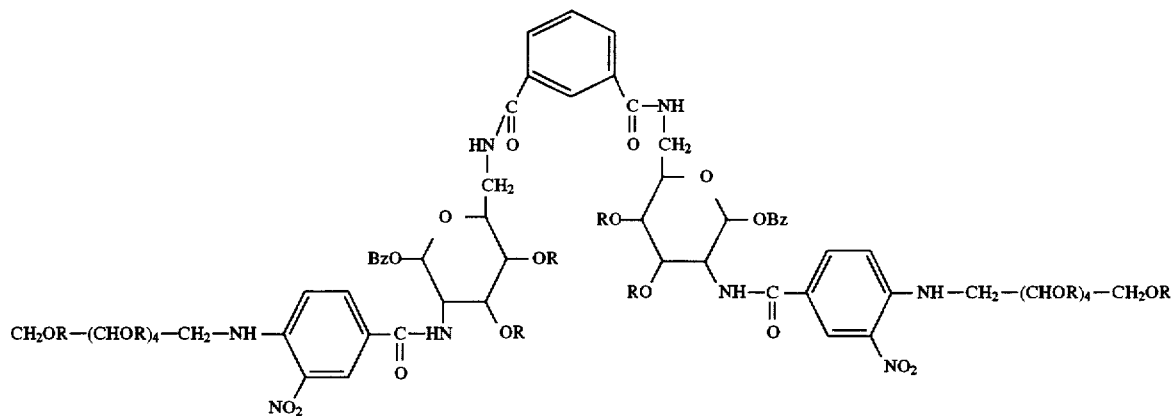

Bz = benzyl            R = SO₃Na 2,7-Bis-[benzyl 2,6-didesoxy-2-[3-nitro-4-(2,3,4,5,6-penta-O-sulfo-D-glucit-1-ylamino)-benzoylamino]-3,4-di-

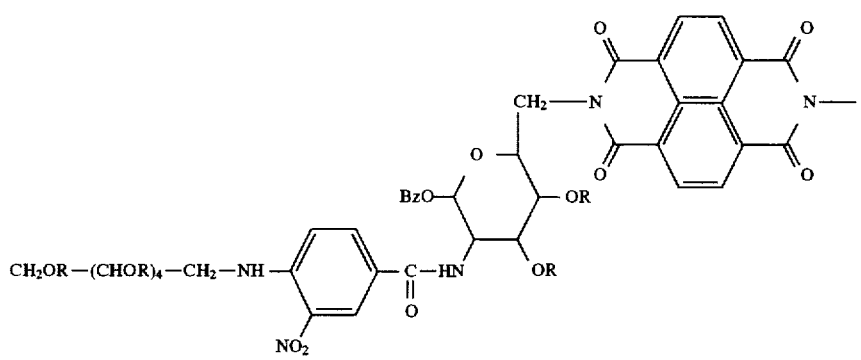

Bz = benzyl

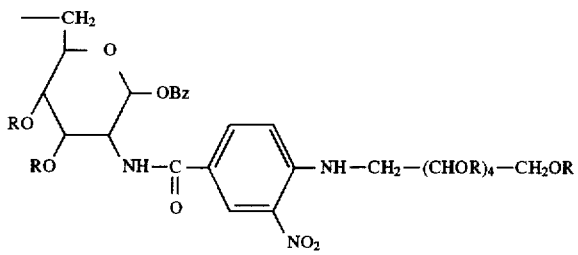

R = SO₃Na

Isophthalic acid bis-[[benzyl 2,6-didesoxy-2-[4-[methyl (2,3,4,5,6-penta-O-sulfo-D-glucit-1-yl)-amino]-3-nitro-benzoylamino]-3,4-di-O-sulfo-a-D-glucopyranosid-6-yl]-amide] tetradecasodium salt (Example 35).

glucit-1-yl)-amino]-3-nitro-benzoylamino]-3,4-di-O-sulfo-a-D-glucopyranosid-6-yl]-amide] hexadecasodium salt (Example 36).

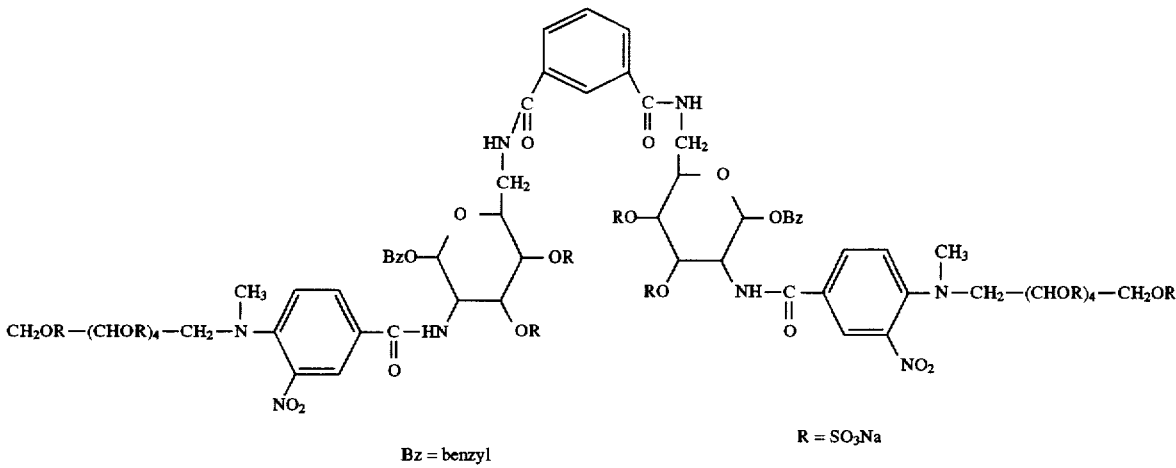

Bz = benzyl

R = SO₃Na

Isophthalic acid bis-[[benzyl 2,6-didesoxy-2-[4-[(2-hydroxysulfonyloxy-ethyl)-2,3,4,5,6-penta-O-sulfo-D-

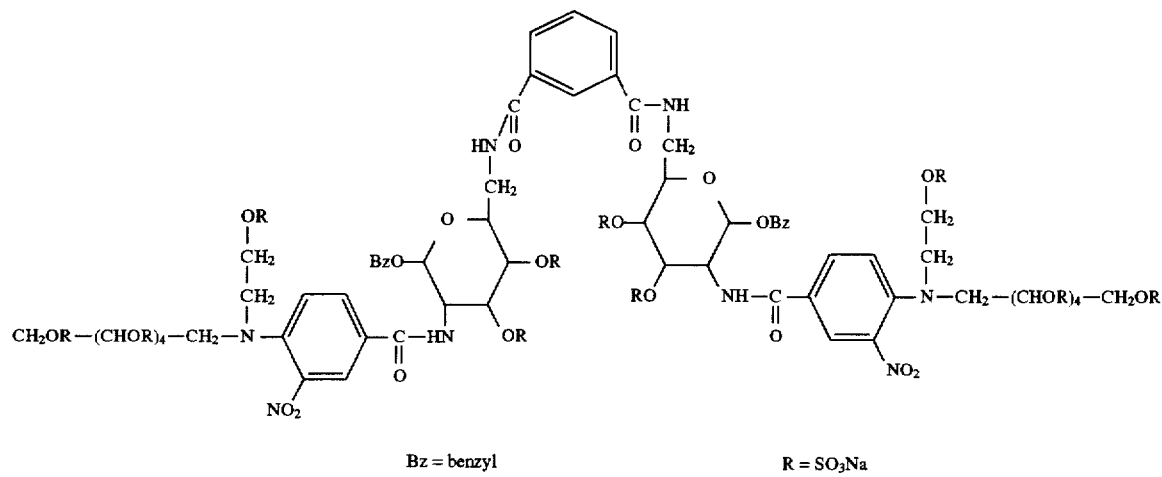

Isophthalic acid bis-[[benzyl 2-[3-acetylamino-4-[methyl-(2,3,4,5,6-penta-O-sulfo-D-glucit-1-yl)-amino]-benzoylamino]-2,6-didesoxy-3,4-di-O-sulfo-a-D-glucopyranosid-6-yl]-amide] tetradecasodium salt (Example 37).

Isophthalic acid bis-[[benzyl 2-[3-acetylamino-4-amino]-benzoylamino]-2,6-didesoxy-3,4-di-O-sulfo-a-D-glucopyranosid-6-yl]-amide] hexadecasodium salt (Example 38).

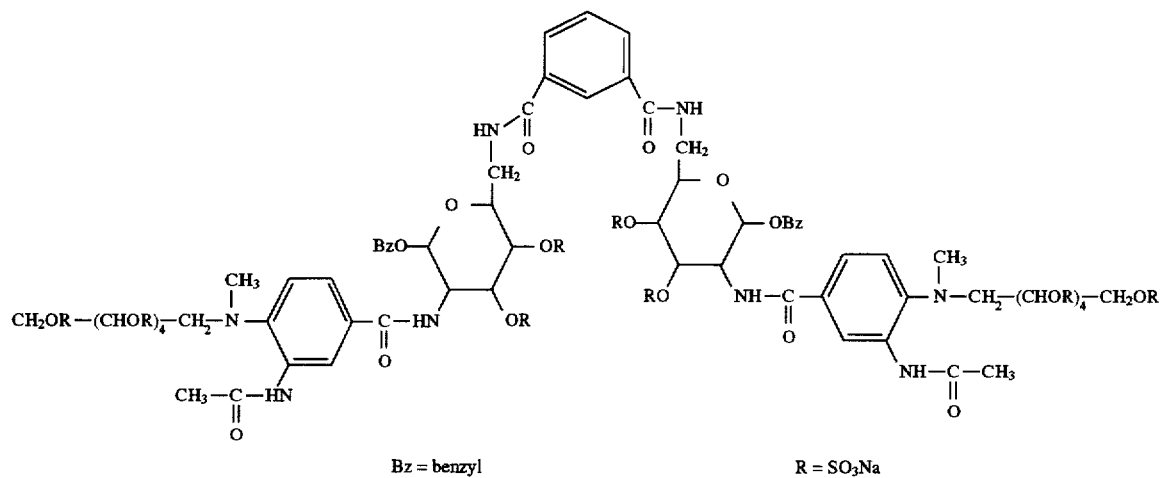

Isophthalic acid bis-[[benzyl 2-[3-acetylamino-4-[(2,3,4,5,6-penta-O-sulfo-D-glucit-1-yl)-(2-sulfonyloxy-ethyl)-

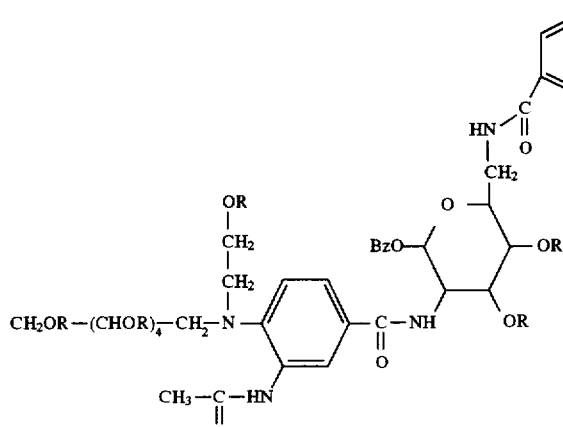
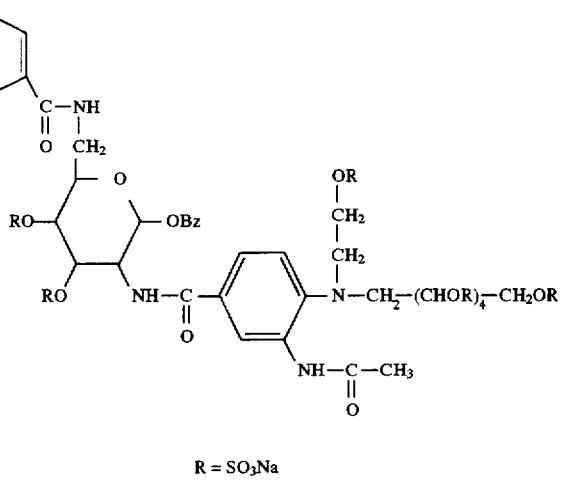

Bz = benzyl

R = SO₃Na

N-[Benzyl 2,6-didesoxy-2-[4-(2,3,4,5,6-penta-O-sulfo-D-glucit-1-ylamino)-3-nitro-benzoylamino]-3,4-di-O-sulfo-a-D-glucopyranosid-6-yl]-N'-[(benzyl 2,6-didesoxy-6-(2,3,4,5,6-penta-O-sulfo-D-gluconylamino)-3,4-di-O-sulfo-a-D-glucopyranosid-2-yl]-isophthalamide tetradecasodium salt (Example 39) is an example of an unsymmetric compound which contains a glycopyranoside residue of formula d) and a glycopyranoside residue of formula f).

The compounds defined earlier can be manufactured in accordance with the invention by reacting a corresponding non-sulfated compound with a sulfating agent.

The sulfation, that is, the esterification with sulfuric acid, in accordance with the invention can be carried out using methods which are known per se for the sulfation of hydroxy groups.

Examples of sulfating agents are $SO_3$ complexes such as $SO_3$·pyridine, $SO_3$·trimethylamine, $SO_3$-dioxan and $SO_3$·dimethylformamide. Further examples of sulfating agents are chlorosulfonic acid, mixtures of chlorosulfonic acid and sulfuric acid, and piperidine N-sulfate.

The reaction is conveniently effected in a suitable solvent, especially a polar solvent, such as dimethylformamide, dimethyl sulfoxide or hexamethylphosportriamide. The reaction can be carried out at room temperature or at an elevated temperature, for example at 20°–70° C., whereby the degree of sulfation can be influenced by varying the reaction duration and temperature. The degree of sulfation achieved in each case can be determined by HPLC. In a preferred embodiment, all or practically all free hydroxy groups are sulfated by suitable choice of reaction duration and temperature. The working up of the reaction mixture and, respectively, the isolation of the reaction product of formula Ia–Ic can be effected according to known methods, for example, by gel filtration or ultrafiltration. Conveniently, the reaction mixture is treated, prior to the working up, with a compound which is sufficiently basic to be capable of forming a salt with the sulfonic acid groups in the compound of formulas Ia–Ic, for example, with an alkali metal acetate, such as sodium acetate, and the compound of formulas Ia–Ic is isolated in salt form, such as the sodium salt.

The starting materials for the process in accordance with the invention, that is, the non-sulfated compounds corresponding to the compounds of formulas Ia–Ic, can be prepared as described in the Examples hereinafter or in analogy thereto. The starting materials for compounds of formulas Ia–Ic can be prepared in general as follows:

As the amino sugar there can be used either commercially available amino sugars such as glucosamine or galactosamine, or an amino function can be introduced according to known methods. Thus, a hydroxyl group of a pyranose can be activated by transformation into a sulfonate or a halide and then converted into the amine directly or via the intermediary introduction of an azide. The anomeric position of the pyranose is conveniently protected by transformation into a pyranoside, which can be effected by Fischer glycosidation or other glycoside synthesis methods.

The free amino function of the amino sugar is reacted with a central alkyl or aryl building brick. When the linkage reaction comprises the formation of an amide bond, then this can be effected by reacting the amino sugar with the central building brick in the form of an ester, lactone, an acid chloride or an acid function activated according to methods known in peptide chemistry (mixed anhydride or active ester). Imides can be obtained analogously by using anhydrides of the central building brick.

The amino sugars can be extended after further functionalization. One possibility for this comprises introducing a further amino function, which can be achieved according to procedures which are known and which are described above. Another possibility comprises introducing an acid functionality; this can be achieved by alkylating a hydroxyl group present with an acid equivalent. The thus-obtained acid derivatives of amino sugars, after activation as described above, can be reacted with suitable cyclic or open-chain derivatives of amino sugars or aminoglycitols. Alternatively, amino sugars which are extended by an amino function can be reacted with hydroxylated lactones with the formation of amides.

The compounds in accordance with the invention inhibit the migration and proliferation of smooth muscle cells of the vascular wall. They can thus be used for the treatment and/or prophylaxis of artereosclerotic changes to the vascular wall, especially for the prevention of restenosis after coronary or peripheral angioplasty or after bypass operations. In principle, these compounds can be used for the treatment and/or prophylaxis of all disorders in which migration or proliferation of smooth muscle cells plays a role.

In contrast to heparin, these compounds have no $AT_{III}$ activity (antithrombin III) and therefore no inhibiting effect on coagulation factors Ia and Xa. Accordingly, their blood coagulation-inhibiting activity is very much lower than that of heparin and thus the risk of bleeding in the case of therapy with these compounds is minimal.

Since heparin-binding proteins play an important role in various disorders, heparin-like substances such as the compounds in accordance with the invention can, in addition, also be used for the treatment of these disorders: for example, invasion by various viruses (Herpes, HIV) is inhibited by such substances, arterial thrombosis (vWF, platelet adhesion) is inhibited by such substances, activation of the complementary system (e.g. in the case of reperfusion) can be diminished and various growth factors or cytokines (e.g. bFGF in tumours) can be inhibited.

The pharmacological activities of the compounds in accord- ance with the invention can be demonstrated in the test proced- ures described hereinafter:

Antiproliferative Activity

The antiproliferative activity of a substance is expressed as the $r_i$ value which is a comparative value to the corresponding activity of heparin and which was determined in cell cultures as follows: rat smooth muscle cells were applied to cell culture plates in a density of $8 \times 10^3$ cells/well (medium: DMEM with 10% FCS. Cultivation at 37° C. and 5% $CO_2$). After 4 hours, the number of adhered cells was determined and the substances to be tested (100 µg/ml, dissolved in $H_2O$) were added. The controls were a) cells to which test compound was not added and b) cells which had been treated with heparin (100 µg/ml). Subsequently, the cells were incubated for 48 h. and thereafter the cell count was determined once more.

The inhibition i of the cell growth, that is, the reduction in the growth rate of the cells in percent compared to the control, was calculated from these values.

$$i = 100 - \frac{\mu \text{substance}}{\mu \text{control}} \cdot 100$$

the growth rate µbeing calculated as $$\mu = \frac{\Delta \ln Z}{\Delta t_{[d]}} = \ln \frac{Z_{(t2)}}{Z_{(t1)}} * \frac{1}{\Delta t_{[d]}} \ [d^{-1}]$$

in which Z is the number of cells and d is the time in days.

Finally, $r_i$—the relative inhibitory activity—which expresses the activity of a substance (at 100 µg/ml) in comparison to the activity of heparin in the same concentration in the same experiment, was calculated:

$$r_i = \frac{i \text{ substance}}{i \text{ heparin}}$$

Blood Coagulation Inhibition

The blood coagulation-inhibiting activity was determined as follows:

*Inhibition of thrombin or Factor Xa in the Chromogen Substrate Test* (Teien et al., Thrombosis Research 10, 399–410 (1977)): The determination was effected in a Cobas-Bio centrifugal automatic spectrophotometer. The buffer solution used consisted of 50 mM Tris buffer, 180 mM NaCl, 7.5 mM EDTA $Na_2$, 1% PEG 6000 and 0.02% Tween 80, pH 8.4. The test solution consisted of 50 µl of buffer, 30 µl of antithombin III (1U/ml, Kabi Diagnostica) and 20 µl of plasma which contained various concentrations of test compounds. 30 µl of sample solution and 20 µl of water with 180 µl of thrombin (1U/ml, Thrombin Reagent Roche Basle) were added to the test cuvette in the automatic analyzer. After incubation at 37° C. for 240 seconds, 60 µl of S-2238 (H-D-Phe-Pip-Arg-NH.pNA, Kabi Diagnostica, Mondal, Sweden, 0.75 mM in water) and 20 µl of water were added. The liberation of pNA (p-nitro-aniline) was followed during 60 seconds at 405 nm in 10 second intervals in comparison to water as the blank. The inhibitory activity is given as the $IC_{50}$, that is, as the concentration [µg/ml] at which the amidolytic activity of thrombin is reduced by 50% in comparison to the plasma control value.

The inhibition of Factor Xa was measured in the same manner using a solution of Factor Xa (2.8 nkat/ml and 2 mM S-2222 (Bz-CO-Ile-Glu-Arg-NH.pNA, Kabi Diagnostica) in water in place of thrombin and, respectively, S-2238.

The activity data obtained in the previously described test procedures with a representative number of compounds of formulas Ia–Ic are given in the following Table:

| Example | Antiproliferative Activity $r_i$ | Anticoagulative Activity $IC_{50}$ [µg/ml] | |
|---|---|---|---|
| | | Thrombin | Factor Xa |
| 11 | 1.7 | >1000 | >1000 |
| 14 | 1.2 | >1000 | >1000 |
| 15 | 1.8 | >1000 | >1000 |
| 23 | 1.8 | >1000 | >1000 |
| 30 | 1.6 | >1000 | >1000 |
| 32 | 1.4 | >1000 | >1000 |
| 33 | 1.5 | >1000 | >1000 |
| 34 | 3.9 | >1000 | >1000 |
| 35 | 2.5 | >1000 | >1000 |
| 36 | 2.1 | >1000 | >1000 |
| 37 | 1.9 | >1000 | >1000 |
| 38 | 1.8 | >1000 | >1000 |
| Heparin | 1.0 | 1.9 | 2.7 |

In vivo assay for the determination of the antiproliferative activity of the compounds in accordance with the invention in damaged rat carotids After narcosis, the left carotids of male Wistar Kyoto rats (300–400 g) were damaged with a 2 F embolectomy catheter by drawing the catheter in the pumped-up state three times through the vessel. After wound healing, the animals were kept in pairs with standard feed and water ad libidum.

The compounds were administered in concentrations of 0.3–1 mg/kg/h i.v. For this purpose, during the narcosis an osmotic minipump was implanted into the animals under the dorsal skin and was attached to the jugular vein. Thus, the compounds could be administered constantly during the entire test period of 14 days.

After 14 days proliferative tissue (neointima) had formed, the size of which could be determined morphometrically on histological cross-sections. For this purpose, the rats were sacrificed and perfusion-fixed with glutaraldehyde.

After i.v. administration of the compound of Example 14 (1 mg/kg/h) the cross-sectional area of the neointima in rat carotids 14 days after balloonisation was significantly reduced (p<0.001 t-test; the number of animals n as given in FIG. 1; average ±SEM).

Figure 2:
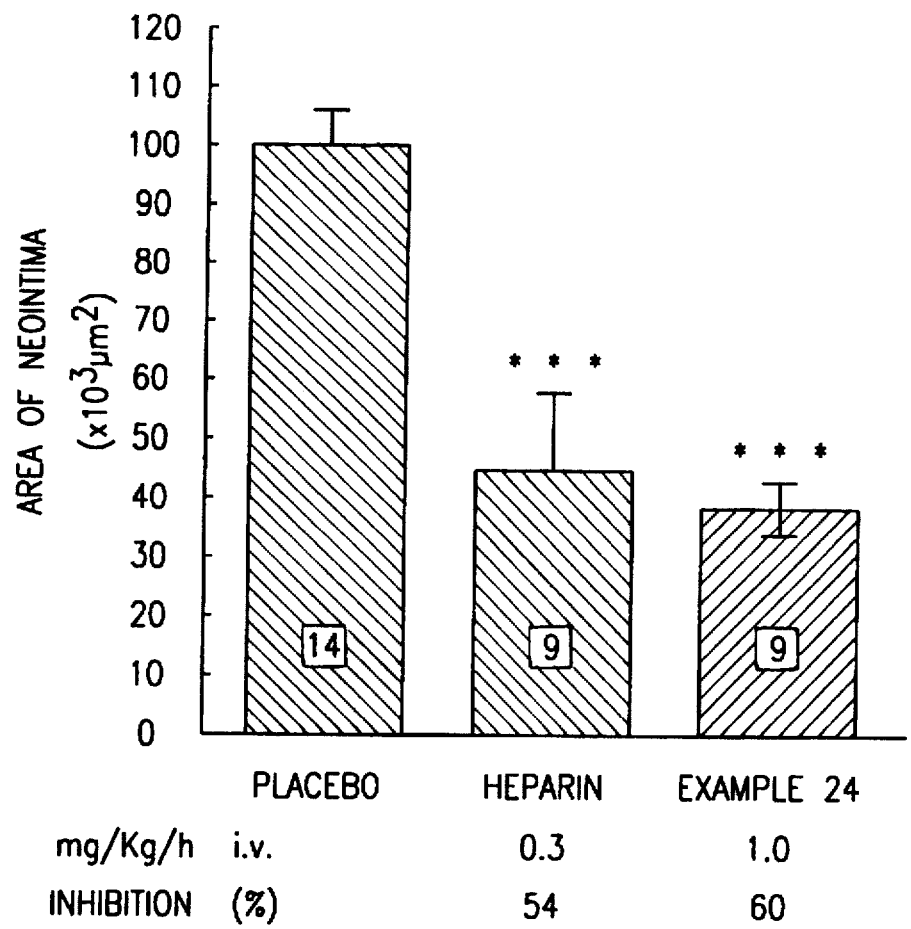

After i.v. administration of the compound of Example 24 (1 mg/kg/h) the cross-sectional area of the neointima in rat carotids 14 days after balloonisation was significantly reduced (p<0.001 t-test; n as given in FIG. 2; average ±SEM).

The test results show that the compounds in accordance with the invention have an antiproliferative activity which corresponds to (or approaches) or is greater than that of heparin, but in contrast to heparin do not exhibit or exhibit a much lower anti-coagulation activity.

The medicaments based on the compounds in accordance with the invention can be administered enterally, for example orally in the form of tablets, coated tablets, dragées, hard and soft gelatin capsules, solutions, emulsions or suspensions, or rectally, for example, in the form of suppositories. However, the administration is preferably effected parenterally, for example, in the form of injection solutions.

For the production of tablets, coated tablets, dragées and hard gelatin capsules the active ingredient can be mixed with pharmaceutically inert, inorganic or organic excipients. Lactose, corn starch or derivatives thereof, talc, stearic acid or its salts can be used for example, as such excipients for tablets, dragées and hard gelatin capsules. Suitable excipients for soft gelatin capsules are for example, vegetable oils, waxes, fats, semi-solid and liquid polyols; depending on the nature of the active ingredient no excipients are, however, usually required in the case of soft gelatin capsules. Suitable excipients for the production of solutions and syrups are for example, water, polyols, sucrose, invert sugar and glucose, suitable excipients for injection solutions are for example, water, alcohols, polyols, glycerol and vegetable oils and suitable excipients for suppositories are for example, natural or hardened oils, waxes, fats and semi-liquid or liquid polyols.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. In the case of enteral administration the resorption of the active ingredient can be increased with the aid of liposomes.

The dosage of the active ingredient can vary within wide limits and will, of course, be fitted to the individual requirements in each particular case. In general, in the case of parenteral administration a dosage of about 0.1 to 100 mg/kg, preferably of about 1.5 to 15 mg/kg, per day should be appropriate for adults, although the upper limit just given can also be exceeded when this is shown to be indicated.

The invention is illustrated further by the following Examples.

EXAMPLE 1

A. A solution of 193 mg of malonic acid and 1.11 g of O-(1,2-dihydro-2-oxo-pyridyl)-1,1,3,3-tetramethyluronium tetrafluoro-borate in 5 ml of dimethylformamide was treated with 0.77 ml of triethylamine at 0° C. After 90 minutes at room temperature, a solution of 1.0 g of benzyl 2-amino-2-desoxy-a-D-glucopyrano-side (Meyer zu Reckendorf, Chem. Ber. 107, 869 (1974)) in 10 ml of dimethylformamide was added and the mixture was stirred at 95° C. for 18 hours. After concentration, the residue was chromatographed over silica gel with ethyl acetate/methanol/ water and gave N,N'-bis-(benzyl-2-desoxy-a-D-glucopyranosid-2-yl)-malonamide. MS: m/z 669.4 ([M+H]$^+$).

B. A solution of 360 mg N,N'-bis-(benzyl 2-desoxy-a-D-glucopyranosid-2-yl)-malonamide in 2.5 ml of dimethylform-amide was treated with 991 mg of sulfur trioxide-trimethylamine complex and stirred at 70° C. for 18 hours. Then, the mixture was treated with 11.7 ml of 10% aqueous sodium acetate solution and evaporated, and the residue was taken up in water and evaporated. The residue was purified by chromatography over Sephadex LH 20 and C25 (Na$^+$) and gave N,N'-bis-(benzyl 2-desoxy-3,4,6-tri-O-sulfo-a-D-glucopyranosid-2-yl)-malonamide hexasodium salt, [a]+96.5° (c 0.2; water). MS: m/z 1218 (reconstructed M).

EXAMPLE 2

A. A suspension of 332 mg of terephthalic acid in 5 ml of tetrahydrofuran and 5 ml of acetonitrile was treated at 0° C. with 0.62 ml of triethylamine and 0.624 ml of isobutyl chloroformate. A solution of 1.35 g of benzyl 2-amino-2-desoxy-a-D-gluco-pyranoside in 4 ml of water and 2 ml of acetonitrile was added to the resulting solution. After stirring at room temperature for 2 hours the mixture was concentrated. The residue was treated with 40 ml of pyridine and 20 ml of acetic anhydride and, after 18 hours at room temperature, concentrated. The residue was chromatographed over silica gel with ethyl acetate/hexane and gave N,N'-bis-(benzyl 3,4,6-tri-O-acetyl-2-desoxy-a-D-glucopyranosid-2-yl)-terephthalamide, [α]+144.0° (c 0.2; dioxan). MS: m/z 921.7 ([M+H]$^+$).

B. A solution of 1.2 g of N,N'-bis-(benzyl 3,4,6-tri-O-acetyl-2-desoxy-a-D-glucopyranosid-2-yl)-terephthalamide in 120 ml of methanol was stirred at room temperature for 3 hours with 9 ml of a 0.3M sodium methanolate solution. The resulting precipitate was washed neutral with methanol, dried and gave N,N'-bis-(benzyl 2-desoxy-a-D-glucopyranosid-2-yl)-terephthalamide. MS: m/z 669.4 ([M+H ]$^+$).

C. Sulfation of N,N'-bis-(benzyl 2-desoxy-a-D-glucopyranosid-2-yl)-terephthalamide as described in Ex. 1 .B. gave N,N'-bis-(benzyl 2-desoxy-3,4,6-tri-O-sulfo-α-D-glucopyranosid-2-yl)-terephthalamide hexasodium salt, [α]+52.5° (c 0.2; water). MS: m/z 1280 (reconstructed M).

EXAMPLE 3

A. Benzyl 2-amino-2-desoxy-a-D-glucopyranoside was reacted with 4,4'-biphenyldicarboxylic acid as described under Ex. 2.A. and gave biphenyl-4,4'-dicarboxylic acid bis-[(benzyl 3,4,6-tri-O-acetyl-2-desoxy-α-D-glucopyranosid-2-yl)-amide], [α]+177.0° (c0.2; dioxan). MS: m/z 997.8 ([M+H]$^+$).

B. Biphenyl-4,4'-dicarboxylic acid bis-[(benzyl 3,4,6-tri-O-acetyl-2-desoxy-a-D-glucopyranosid-2-yl)-amide] was deacetylated as described in Ex. 2.B. and gave biphenyl-4,4'-dicarboxylic acid bis-[(benzyl 2-desoxy-α-D-glucopyranosid-2-yl)-amide]. MS: m/z 743.6 ([M−H]$^-$).

C. A suspension of 750 mg of biphenyl-4,4'-dicarboxylic acid bis-[(benzyl 2-desoxy-α-D-glucopyranosid-2-yl)-amide] in 20 ml of dimethylformamide was treated with 2.7 g of sulfur trioxide-trimethylamine complex and stirred at 65° C. for 3 days. Then, the mixture was treated with 40 ml of 10% aqueous sodium acetate solution and evaporated, and the residue was taken up in water and evaporated. The residue was purified by chromatography over Sephadex LH 20 and C25 (Na$^+$) and gave biphenyl-4,4'-dicarboxylic acid bis-[(benzyl 2-desoxy-3,4,6-tri-O-sulfo-α-D-glucopyranosid-2-yl)-amide] hexasodium salt, [α]+105.0° (c 0.2; water). MS: m/z 1356 (reconstructed M).

EXAMPLE 4

A. A suspension of 750 mg of biphenyl-4,4'-dicarboxylic acid bis-[(benzyl 2-desoxy-α-D-glucopyranosid-2-yl)-amide (see Ex. 3.B.) in 20 ml of dimethylformamide was treated with 1.68 g of sulfur trioxide-trimethylamine complex and stirred at 70° C. for 18 hours. Then, the mixture was treated with 19.9 ml of 10% aqueous sodium acetate solution and evaporated, and the residue was taken up in water and evaporated. The residue was purified by chromatography over Sephadex LH 20 and C25 (Na$^+$) and gave biphenyl-4,4'-dicarboxylic acid bis-[(benzyl 2-desoxy-3,6-di-O-sulfo-α-D-glucopyranosid-2-yl)-amide] tetrasodium salt, [α]+102.5° (c 0.2; water). MS: m/z 1152 (reconstructed M).

EXAMPLE 5

A. Benzyl 2-amino-2-desoxy-α-D-glucopyranoside was reacted with naphthalene-1,4-dicarboxylic acid as described under Ex. 2.A. and gave naphthalene-1,4-dicarboxylic acid bis-[(benzyl 3,4,6-tri-O-acetyl-2-desoxy-α-D-glucopyranosid-2-yl)-amide], [α]+153.5° (c 0.2; dioxan). MS: m/z 971.6 ([M+H]$^+$).

B. Naphthalene-1,4-dicarboxylic acid bis-[(benzyl 3,4,6-tri-O-acetyl-2-desoxy-α-D-glucopyranosid-2-yl)-amide] was deacetyl-ated as described in Ex. 2.B. and gave naphthalene-1,4-dicar-boxylic acid bis-[(benzyl 2-desoxy-α-D-glucopyranosid-2-yl)-amide], MS: m/z 719.4 ([M+H]$^+$).

C. Sulfation of naphthalene-1,4-dicarboxylic acid bis-[(benzyl 2-desoxy-α-D-glucopyranosid-2-yl)-amide] as described in Ex. 1.B. gave naphthalene-1,4-dicarboxylic acid bis-[(benzyl- 2-desoxy-3,4,6-tri-O-sulfo-α-D-glucopyranosid-2-yl) - amide] hexasodium salt, [α]+133.5° (c 0.2; water), MS: m/z 1330 (reconstructed M).

EXAMPLE 6

A. Benzyl 2-amino-2-desoxy-α-D-glucopyranoside was reacted with naphthalene-2,6-dicarboxylic acid as described under Ex. 2.A. and gave (naphthalene-2,6-dicarboxylic acid bis-[(benzyl 3,4,6-tri-O-acetyl-2-desoxy-α-D-glucopyranosid-2-yl)-amide], [α]+175.0° (c 0.2; dioxan). MS: m/z 971.4 ([M+H]$^+$).

B. A solution of 1.0 g of (naphthalene-2,6-dicarboxylic acid bis- [(benzyl 3,4,6-tri-O-acetyl-2-desoxy-α-D-glucopyranosid-2-yl)-amide] in 20 ml of methanol and 20 ml of dioxan was stirred at room temperature for 18 hours with ml of a 0.3M sodium methanolate solution. The resulting precipitate was washed with methanol, dioxan and ether, dried and gave naphthalene-2,6-dicarboxylic acid bis-[(benzyl 2-desoxy-α-D-glucopyranosid-2-yl)-amide], MS: m/z 717.2 ([M−H]$^−$).

C. Sulfation of naphthalene-2,6-dicarboxylic acid bis-[(benzyl 2-desoxy-α-D-glucopyranosid-2-yl)-amide] as described in Ex. 1.B. gave naphthalene-2,6-dicarboxylic acid bis-[(benzyl 2-desoxy-3,4,6-tri-O-sulfo-α-D-glucopyranosid-2-yl)-amide] hexasodium salt, [α]+117.0° (c 0.2; water), MS: m/z 1330 (reconstructed M).

EXAMPLE 7

A. Benzyl 2-amino-2-desoxy-α-D-glucopyranoside was reacted with (E)-stilbene-4,4'-dicarboxylic acid as described under Ex. 2.A. and gave (E)-stilbene-4,4'-dicarboxylic acid bis-[(benzyl 3,4,6-tri-O-acetyl-2-desoxy-α-D-glucopyranosid-2-yl)-amide], [α]+195.0° (c 0.2; dioxan). MS: m/z 1023.4 ([M+H]$^+$).

B. (E)-Stilbene-4,4'-dicarboxylic acid bis-[(benzyl 3,4,6-tri-O-acetyl-2-desoxy-α-D-glucopyranosid-2-yl)-amide] was deacetylated as described in Ex. 6.B. and gave (E)-stilbene-4,4'-dicarboxylic acid bis-[(benzyl 3,4,6-tri-O-acetyl-2-desoxy-α-D-glucopyranosid-2-yl)-amide], MS: m/z 769.2 ([M−H]$^−$).

C. Sulfation of (E)-stilbene-4,4'-dicarboxylic acid bis-[(benzyl 3,4,6-tri-O-acetyl-2-desoxy-α-D-glucopyranosid-2-yl)-amide] as described in Ex. 1.B. gave (E)-stilbene-4,4'-dicarboxylic acid bis-[(benzyl 2-desoxy-3,4,6-tri-O-sulfo-α-D-glucopyranosid-2-yl)-amide] hexasodium salt, [α]+131.0° (c 0.2; water), MS: m/z 1382 (reconstructed M).

EXAMPLE 8

A. A solution of 300 mg of N,N'-bis-(benzyl 2-desoxy-3,4,6-tri-O-sulfo-α-D-glucopyranosid-2-yl)-terephthalamide hexasodium salt (see Ex. 2.C.) in 10 ml of water was hydrogenated at room temperature in the presence of palladium on charcoal for 16 hrs. After filtration over a filter aid, the filtrate was concentrated and the residue was purified by chromatography over Sephadex LH 20 20 to give N,N'-bis-(2-desoxy-3,4,6-tri-O-sulfo-D-glucopyranos-2-yl)-terephthalamide hexasodium salt, MS: m/z 1100 (reconstructed M).

EXAMPLE 9

A. A solution of 30 g of benzyl 2-benzyloxycarbonylamino-2-desoxy-α-D-glucopyranoside (Heyns and Paulsen, Chem. Ber. 88, 188 (1955)) in 116 ml of pyridine was treated at 0° C. with a solution of 19.85 g of p-tolylsulfonyl chloride in 30 ml of 30 dichloromethane and stirred at room temperature for 4 hours. Then, the mixture was poured into ice-cold 2N sulfuric acid and extracted with dichloromethane. The organic phases were washed with aqueous sodium hydrogen carbonate solution, dried over magnesium sulfate and concentrated. The residue was chromatographed over silica gel with hexane/ethyl acetate and gave benzyl 2-benzyloxycarbonylamino-2-desoxy-6-O-(p-tolylsulfonyl)-α-D-glucopyranoside, [α]+101.80 (c 0.5; dioxan), MS: m/z 580 ([M+Na]$^+$).

B. A solution of 32.14 g of benzyl 2-benzyloxycarbonylamino-2-desoxy-6-O-(p-tolylsulfonyl)-α-D-glucopyranoside in 75 ml of dimethyl sulfoxide was treated at room temperature with 7.5 g of sodium azide and stirred at 90°C. for 3 hours. The mixture was then poured on to ice/water. Separated crystals were filtered off under suction, washed with water and dried. There was obtained benzyl 6-azido-2-benzyloxycarbonylamino-2,6-didesoxy-α-D-glucopyranoside, [α]+119.6° (c 0.5; dioxan), MS: m/z 428 ([M+H]$^+$).

C. A solution of 1.1 g of benzyl 6-azido-2-benzyloxycarbonyl-amino-2,6-didesoxy-α-D-glucopyranoside in 7.5 ml of tetra-hydrofuran and 69 ml of water was treated at room temperature with 674 mg of triphenylphosphine and stirred for 24 hours.

Then, 1 ml of water was added to the thick slurry and the mixture was stirred for a further 30 minutes and concentrated.

The residue was crystallized from methanol and gave benzyl 6-amino-2-benzyloxycarbonylamino-2,6-didesoxy-α-D -glucopyranoside, [α]+124.20 (c 0.6; acetone), MS: m/z 403 ([M+H]$^+$).

D. A solution of 1.07 g of 1,2-O-isopropylidene-α-D-glucouranurono-6,3-lactone (Weidmann, Ann. 679, 178 (1964)) in 10 ml of tetrahydrofuran was treated at 10° C. with a suspension of 2.0 g of benzyl 6-amino-2-benzyloxycarbonylamino-2,6-didesoxy-α-D-glucopyranoside in 30 ml of tetrahydrofuran and stirred at room temperature for 3.5 hours. After the addition of 0.5 g of 1,2-O-isopropylidene-α-D-glucofuranurono-6,3-lactone, the mixture was stirred at 50° C. for a further 7 hours and then concentrated. The residue was dissolved in 15 ml of pyridine at 0° C., treated with 2.64 ml of benzoyl chloride and held at room temperature for 18 hours. The reaction solution was poured on to ice/water and extracted with ethyl acetate. The organic phases were washed with water, dried over sodium sulfate and, after concentration, the residue was chromatographed over silica gel with toluene/ethyl acetate. The product fractions gave benzyl 3,4-di-O-benzoyl-6-[(3,5-di-O-benzoyl-1,2-O-isopropylidene-α-D -glucofuranuronyl)-amino]-2-benzyloxycarbonylamino-2,6-didesoxy-α-D-glucopyranoside, [α]+14.0° (c 0.5; dioxan), MS: m/z 1035.6 ([M+H]$^+$)

E. A solution of 0.75 g of benzyl 3,4-di-O-benzoyl-6-[(3,5-di-O-benzoyl-1,2-0-isopropylidene-α-D-glucofuranuronyl)-amino]-2-benzyloxycarbonylamino-2,6-didesoxy-α-D-glucopyranoside in 10 ml of methanol was hydrogenated at room temperature in the presence of palladium on charcoal (10%). After 5 hours, the catalyst was filtered off, the filtrate was concentrated and the residue was chromatographed over silica gel with hexane/ethyl acetate. The product fractions gave benzyl 2-amino-3,4-di-O-benzoyl-6-(3,5-di-O-benzoyl-1,2-0-isopropylidene-α-D-glucofuranuronyl)-amino-2,6-didesoxy-α-D-glucopyranoside. MS: m/z 901.5 ([M+H]$^+$).

F. A solution of 218 mg of biphenyl-4,4'-dicarboxylic acid in 15 ml of tetrahydrofuran and 15 ml of acetonitrile was treated with 0.279 ml of triethylamine and 0.232 ml of isobutyl chloroformate at −10°C. and stirred at this temperature for 30 minutes. Then, a solution of 1.62 g of benzyl 2-amino-3,4-di-O-benzoyl-6-[(3,5-di-O-benzoyl-1,2-O-isopropylidene-α-D-glucofuranuronyl)-amino]-2,6-didesoxy-α-D-glucopyranoside in 10 ml of tetrahydrofuran and 10 ml of acetonitrile was added and the mixture was stirred at room temperature for 5 hours. After concentration, the residue was chromatographed over silica gel with dichloromethane/ethyl acetate and gave biphenyl-4,4'-dicarboxylic acid bis-[[benzyl 3,4-di-O-benzoyl-6-[(3,5-di-O-benzoyl-1,2-O-isopropylidene-α-D-glucofuranuronyl)-amino]-2,6-didesoxy-α-D-glucopyranosid-2-yl]-amide]. [α]+80.0° (c 0.2; dioxan). MS: m/z 2029.6 ([M+Na]$^+$).

G. A solution of 450 mg of biphenyl-4,4'-dicarboxylic acid bis-[[benzyl 3,4-di-O-benzoyl-6-[(3,5-di-O-benzoyl-1,2-O-isopropylidene-α-D-glucofuranuronyl)-amino]-2,6-didesoxy-α-D-glucopyranosid-2-yl]-amide] in 8 ml of methanol and 4 ml of dioxan was stirred at room temperature for 4 hours with 0.5 ml of a 0.3M sodium methanolate solution. The resulting precipitate was dissolved in methanol. The solution was made neutral with acidic ion exchanger (Amberlite IR 120 H$^+$) and concentrated. Crystallization from methanol gave biphenyl-4,4'-dicarboxylic acid bis-[[benzyl 2,6-didesoxy-6-(1,2-O-isopropylidene-α-D-glucofuranuronyl)-amino]-α-D-glucopyranosid-2-yl]-amide]. [α]+76.0° (c 0.2; dimethylformamide). MS: m/z 1175.4 ([M+H]$^+$).

H. A solution of 260 mg of biphenyl-4,4'-dicarboxylic acid bis-[[benzyl 2,6-didesoxy-6-(1,2-O-isopropylidene-α-D-glucofuranuronyl)-amino]-α-D-glucopyranosid-2-yl[-amide] in 5 ml of dimethylformamide was treated with 493 mg of sulfur trioxide-trimethylamine complex and stirred at 70° C. for 24 hours. The mixture was then treated with 5.8 ml of 10% aqueous sodium acetate solution and evaporated. The residue was purified by chromatography over Sephadex LH 20 and C25 (Na$^+$) and gave biphenyl-4,4'-dicarboxylic acid bis-[[benzyl 2,6-didesoxy-6-[(1,2-O-isopropylidene-3,5-di-O-sulfo-α-D-glucofuranuronyl)-amino]-3,4-di-O-sulfo-α-D-glucopyranosid-2-yl]-amide] octasodium salt. [α]+61.5° (c 0.2; water). MS: m/z 1991 (reconstructed M).

EXAMPLE 10

A. A solution of 2.0 g of benzyl 6-amino-2-benzyloxycarbonyl-amino-2,6-didesoxy-α-D-glucopyranoside (see Ex. 9.C.) in 30 ml of tetrahydrofuran was treated at 8° C. with a solution of 1.2 g of methyl b-D-glucofuranosidurono-6,3-lactone (Osman et al., J. Am. Chem Soc. 73, 2726 (1951)) in 20 ml of tetrahydrofuran and 10 ml of acetonitrile and stirred at 55° C. under argon for 3.5 hours. After the addition of a total of 1.8 g of methyl b-D-glucofuranosidurono-6,3-lactone, the mixture was stirred at 55° C. for 4 days and then concentrated. The residue was dissolved in 30 ml of pyridine at 0° C., treated with 6.88 ml of benzoyl chloride and held at room temperature for 30 minutes. The reaction solution was treated with ice/water and extracted with ethyl acetate. The organic phases were washed with water, dried over sodium sulfate and, after concentration, the residue was chromatographed over silica gel with hexane/ethyl acetate. The product fractions gave benzyl 3,4-di-O-benzoyl-2-benzyloxy-carbonylamino-2,6-didesoxy-6-[(methyl-2,3,5-tri-O-benzoyl-b-D-glucofuranosiduronyl)-amino]-α-D-glucopyranoside. [α]+27.50 (c5 0.15; dioxan). MS: m/z 1113 ([M+H]$^+$).

B. A solution of 2.6 g of benzyl 3,4-di-O-benzoyl-2-benzyloxycarbonylamino-2,6-didesoxy-6-[(methyl-2,3,5-tri-O-benzoyl-α-D-glucofuranosiduronyl)-amino]-α-D-glucopyranoside in 20 ml of tetrahydrofuran and 2.5 ml of water was hydrogenated at room temperature in the presence of palladium on charcoal (10%). After 4 hours, the catalyst was filtered off over a filter aid, the filtrate was concentrated and the residue was chromatographed over silica gel with hexane/ethyl acetate/2% triethylamine. The product fractions gave benzyl 2-amino-3,4-di-O-benzoyl-2,6-didesoxy-6-[(methyl-2,3,5-tri-O-benzoyl-b-D-glucofuranosid-uronyl)-amino]-α-D-glucopyranoside. [α]+37.5° (c 0.15; Dioxan).MS: m/z 979.5 ([M+H]$^+$).

C. Reaction of benzyl 2-amino-3,4-di-O-benzoyl-2,6-didesoxy-6-[(methyl-2,3,5-tri-O-benzoyl-b-D-glucofuranosiduronyl)-amino]-α-D-glucopyranoside with 4,4'-biphenyldicarboxylic acid as described in Ex. 9.F. gave biphenyl-4,4'-dicarboxylic acid bis-[[benzyl 2,6-didesoxy-3,4-di-O-benzoyl-6-[(methyl-2,3,5-tri-O-benzoyl-b-D-glucofuranosiduronyl)-amino]-α-D-glucopyranosid-2-yl]-amide]. [α]+100.0° (c 0.2; Dioxan). MS: m/z 2169.5 ([M+Na]$^+$).

D. Biphenyl-4,4'-dicarboxylic acid bis-[[benzyl 2,6-didesoxy-3,4-di-O-benzoyl-6-[(methyl-2,3,5-tri-O-benzoyl-b-D-glucofuran-osiduronyl)-amino]-α-D-glucopyranosid-2-yl]-amide] was debenzoylated as described in Ex. 9. G. and gave biphenyl-4,4'-dicarboxylic acid bis-[[benzyl 2,6-didesoxy-6-[(methyl b-D-glucofuranosiduronyl)-amino]-α-D-glucopyranosid-2-yl]-amide]. [α]+48.0° (c 0.2; dioxan). MS: m/z 1124.4 ([M+H]$^+$).

E. Sulfation of biphenyl-4,4'-dicarboxylic acid bis-[[benzyl 2,6-didesoxy-6-[(methyl-b-D-glucofuranosiduronyl)-amino]-α-D-glucopyranosid-2-yl]-amide] as described in Ex. 9.H. gave biphenyl-4,4'-dicarboxylic acid bis-[[benzyl 2,6-didesoxy-6-[(methyl 2,3,5-tri-O-sulfo-b-D-glucofuranosiduronyl)-amino]-3,4-di-O-sulfo-α-D-glucopyranosid-2-yl]-amide] decasodium salt. [α]+56.0° (c 0.2; water). MS: m/z 2143 (reconstructed M).

EXAMPLE 11

A. A suspension of 20.0 g of benzyl 4,6-(R)-O-benzylidene-2-benzyloxycarbonylamino-2-desoxy-α-D-glucopyranoside (Wyss and Kiss, Helv. Chim. Acta 58, 1833 (1975)) in 200 ml of dioxan was treated at room temperature with 6.0 g of powdered potassium hydroxide. 68 ml of tert.-butyl bromoacetate were added dropwise within 10 minutes. After stirring at 55° C. for 2 hours, the reaction mixture was poured on to ice/aqueous sodium hydrogen carbonate solution and extracted with ethyl acetate. The organic phases were washed with water, dried over sodium sulfate and concentrated, and the residue was crystallized from ethyl acetate/hexane. There was obtained benzyl 4,6-(R)-O-benzylidene-2-benzyloxycarbonylamino-3-O-tert.-butoxycarbonylmethyl-2-desoxy-α-D-glucopyranoside, [α]+89.6° (c 0.5; dioxan), MS: m/z 628.5 ([M+Na]⁺).

B. A solution of 3.73 g of benzyl 4,6-(R)-O-benzylidene-2-benzyloxycarbonylamino-3-O-tert.-butoxycarbonylmethyl-2-desoxy-α-D-glucopyranoside in 78 ml of ether was added dropwise at 0° C. to a solution of 5.97 g of potassium tert.-butylate in 112 ml of ether and 0.25 ml of water and the mixture was then heated under reflux for 18 hours. After cooling, the mixture was acidified (pH 5) with 1N HCl, treated with ice/water and extracted with dichloromethane. The organic phases were washed with water, dried over magnesium sulfate and concentrated, and the residue was crystallized from tetrahydrofuran/hexane. There was obtained benzyl 4,6-(R)-O-benzylidene-2-benzyloxycarbonyl-amino-3-O-carboxymethyl-2-desoxy-α-D-glucopyranoside, [α]+103.2° (c 0.5; dioxan), MS: m/z 548.2 ([M−H]⁻).

C. A solution of 4.45 g of benzyl 4,6-(R)-O-benzylidene-2-benzyloxycarbonylamino-3-O-carboxymethyl-2-desoxy-α-D -glucopyranoside in 60 ml of tetrahydrofuran and 60 ml of acetonitrile was treated with 2.49 ml of triethylamine and 2.1 ml of isobutyl chloroformate at −10° C. and stirred at this temperature for 15 minutes. Then, a solution of 1.62 g of benzyl 2-amino-2-desoxy-α-D-glucopyranoside in 10 ml of tetrahydrofuran and 10 ml of acetonitrile was added and the mixture was stirred at room temperature for 3 hours. The reaction mixture was concentrated and acetylated with 10 ml of acetic anhydride in 20 ml of pyridine at room temperature for 18 hours. The mixture was then concentrated and the residue was purified by chromatography over silica gel with ethyl acetate/hexane. There was obtained benzyl 3-O-[(benzyl-3,4,6-tri-O-acetyl-2-desoxy-α- D-glucopyranosid)-2-ylcarbamoylmethyl]-4,6-(R)-O-benzylidene-2-benzyloxycarbonylamino-2-desoxy-α-D-glucopyranoside, [α]+107.4° (c 0.5; dioxan), MS: m/z 927.6 ([M+H]⁺).

D. A solution of 4.5 g of benzyl 3-O-[(benzyl 3,4,6-tri-O-acetyl-2-desoxy-α-D-glucopyranosid)-2-ylcarbamoylmethyl]-4,6-(R)-O-benzylidene-2-benzyloxycarbonylamino-2-desoxy-α-D-glucopyranoside in 45 ml of tetrahydrofuran was hydrogenated at room temperature in the presence of palladium on charcoal (10%). After 5 hours, the catalyst was filtered off over a filter aid and the filtrate was concentrated. There was obtained benzyl 2-amino-3-O-[(benzyl 3,4,6-tri-O-acetyl-2-desoxy-α-D-glucopyranosid)-2-ylcarbamoylmethyl]-4,6-(R)-O-benzylidene-2-desoxy-α-D-glucopyranoside, [α]+146.0° (c 0.2; dioxan), MS: m/z 793.3 ([M+H]⁺).

E. Reaction of benzyl 2-amino-3-O-[(benzyl 3,4,6-tri-O-acetyl-2-desoxy-α-D-glucopyranosid)-2-ylcarbamoylmethyl]-4,6-(R)-O-benzylidene-2-desoxy-α-D-glucopyranoside with biphenyl-4,4'-dicarboxylic acid as described in Ex. 9.F. gave biphenyl-4,4'-di-carboxylic acid bis-[[benzyl 3-O-[(benzyl 3,4,6-tri-O-acetyl-2-desoxy-α-D-glucopyranosid)-2-ylcarbamoylmethyl]-4,6-(R)-O-benzylidene- 2-desoxy-α-D-glucopyranosid-2-yl]-amide], [α]+114.0° (c 0.2; chloroform).

F. A solution of 650 mg of biphenyl-4,4'-dicarboxylic acid bis [[benzyl 3-O-[(benzyl 3,4,6-tri-O-acetyl-2-desoxy-α-D-glucopyranosid)-2-ylcarbamoylmethyl]-4,6-(R)-O-benzylidene-2-desoxy-α-D-glucopyranosid-2-yl]-amide] in 15 ml of methanol was stirred at room temperature for 4 hours with 1.0 ml of a 0.3M sodium methanolate solution. The resulting precipitate was washed with methanol and dried and gave biphenyl-4,4'-di-carboxylic acid bis-[[benzyl 3-O-[(benzyl 2-desoxy-α-D-glucopyranosid)-2-ylcarbamoylmethyl]-4,6-(R)-O-benzylidene-2-desoxy-α-D-glucopyranosid-2-yl]-amide], [α]+136.0° (c 0.2; dimethyl sulfoxide).

G. Sulfation of biphenyl-4,4'-dicarboxylic acid bis-[[benzyl 3-O-[(benzyl 2-desoxy-α-D-glucopyranosid)-2-ylcarbamoylmethyl]-4,6-(R)-O-benzylidene-2-desoxy-α-D-glucopyranosid-2-yl]-amide] as described in Ex. 9.H. gave (biphenyl-4,4'-dicarboxylic acid)-bis-[[benzyl 3-O-[(benzyl 2-desoxy-2,3,4-tri-O-sulfo-α-D-glucopyranosid)-2-ylcarbamoylmethyl]-4,6-(R)-O-benzylidene-2-desoxy-α-D-glucopyranosid-2-yl]-amide] hexasodium salt, [α]+68.0° (c 0.2; dimethyl sulfoxide).

EXAMPLE 12

A. A solution of 300 mg of biphenyl-4,4'-dicarboxylic acid bis-[[benzyl 3-O-[(benzyl 3,4,6-tri-O-acetyl-2-desoxy-α-D-gluco-pyranosid)-2-ylcarbamoylmethyl]-4,6-(R)-O-benzylidene-2-desoxy-α-D-glucopyranosid-2-yl]-amide] in 10 ml of chloroform and 10 ml of dioxan was hydrogenated at room temperature in the presence of palladium on charcoal (10%). After 3 days, the catalyst was filtered off over a filter aid and the filtrate was concentrated. Chromatography over silica gel with ethyl acetate/methanol/water gave biphenyl-4,4'-dicarboxylic acid bis-[[benzyl 3-O-] (benzyl 3,4,6-tri-O-acetyl-2-desoxy-α-D-glucopyranosid-2-ylcarbamoylmethyl)-2-desoxy-α-D-glucopyranosid-2-yl]-amide], [α]+118.5° (c 0.2; chloroform), MS: m/z 1615.5 ([M+H]⁺).

B. A solution of biphenyl-4,4'-dicarboxylic acid bis-[[benzyl 3-O-](benzyl 3,4,6-tri-O-acetyl-2-desoxy-α-D-glucopyranosid-2-ylcarbamoylmethyl)-2-desoxy-α-D-glucopyranosid-2-yl[-amide] in methanol/dioxan 2:1 was deacetylated as described in Ex. 11.F. and gave biphenyl-4,4'-dicarboxylic acid bis-[[benzyl 3-O-(benzyl 2-desoxy-α-D-glucopyranosid-2-ylcarbamoylmethyl)-2-desoxy-α-D-glucopyranosid-2-yl]-amide], MS: m/z 1364.6 ([M+H]⁺).

C. Sulfation of biphenyl-4,4'-dicarboxylic acid bis-[[benzyl 3-O-(benzyl 2-desoxy-α-D-glucopyranosid-2-ylcarbamoylmethyl)-2-desoxy-α-D-glucopyranosid-2-yl]-amide] as described in Ex. 9.H. gave biphenyl-4,4'-dicarboxylic acid bis-[[benzyl 3-O-(benzyl 2-desoxy-3,4,6-tri-O-sulfo-α-D-glucopyranosid-2-ylcarbamoylmethyl)-2-desoxy-4,6-di-O-sulfo-α-D-glucopyranosid-2-yl]-amide] decasodium salt, [α]+73.5° (c 0.2; water), MS: m/z 2384 (reconstructed M).

EXAMPLE 13

A. A solution of 3.0 g of benzyl 4,6-(R)-O-benzylidene-2-benzyloxycarbonylamino-3-O-carboxymethyl-2-desoxy-α-D -glucopyranoside (see Ex. 11.B.) in 20 ml of tetrahydrofuran was treated with 65 mg of N-hydroxysuccinimide and thereafter with a solution of 1.09 g of glucamine in 10 ml of water at room temperature. Then, a solution of 1.24 g of dicyclohexylcarbodiimide in 5ml of tetrahydrofuran was added and the mixture was stirred for 18 hours. The reaction mixture was concentrated and the residue was acetylated with 25 ml of acetic anhydride in 50 ml of pyridine for 18 hours. The reaction mixture was again concentrated and the residue was chromatographed over silica gel with ethyl acetate/toluene to give benzyl 3-O-(2,3,4,5,6-penta-O-acetyl-D-glucit-1-ylcarbamoylmethyl)-4,6-(R)-O-benzylidene-2- benzyloxycarbonylamino-2-desoxy-α-D-glucopyranoside. [α]+28.5° (c 0.2; dioxan). MS: m/z 923.2 ([M+H]⁺).

B. A solution of 250 mg of benzyl 3-O-(2,3,4,5,6-penta-O-acetyl-D-glucit-1-ylcarbamoylmethyl)-4,6-(R)-O-benzylidene-2-benzyloxycarbonylamino-2-desoxy-α-D-glucopyranoside in 20 ml of dioxan and 2 ml of water was hydrogenated at room temperature in the presence of palladium on charcoal (10%). After 2 hours, the catalyst was filtered off over a filter aid and the filtrate was concentrated. After chromatography over silica gel with ethyl acetate/methanol/water/triethylamine, there was obtained benzyl 2-amino-3-O-(2,3,4,5,6-penta-O-acetyl-D-glucit-1-ylcarbamoylmethyl)-4,6-(R)-O-benzylidene-2-desoxy-α-D-glucopyranoside. MS: m/z 789.3 ([M+H]⁺).

C. Reaction of benzyl 2-amino-3-O-(2,3,4,5,6-penta-O-acetyl-D-glucit-1-ylcarbamoylmethyl)-4,6-(R)-O-benzylidene-2-desoxy-α-D-glucopyranoside with terephthalic acid as described in Ex. 9.F. gave N,N'-bis-[benzyl 3-O-(2,3,4,5,6-penta-O-acetyl-D-glucit-1-ylcarbamoylmethyl)-4,6-(R)-O-benzylidene-2-desoxy-α-D-glucopyranosid-2-yl]-terephthalamide. MS: m/z 873.6 ([M+H +K]²⁺/2).

D. A solution of 300 mg of N,N'-bis-[benzyl-3-O-(2,3,4,5,6-penta-O-acetyl-D-glucit-1-ylcarbamoylmethyl)-4,6-(R)-O-benzylidene-2-desoxy-α-D-glucopyranosid-2-yl]-terephthalamide in 10 ml of methanol and 5 ml of dichloromethane was stirred at room temperature with 2 ml of a 0.3M sodium methanolate solution for 18 hours. The resulting precipitate was separated by centrifugation, washed with methanol and dried to give terephthalic acid bis-[[benzyl 4,6-O-benzylidene-2-desoxy-3-O-(D-glucit-1-ylcarbamoylmethyl)-α-D-glucopyranosid-2-yl]-amide]. This product was sulfated as described in Ex. 9H. and gave 1,4-bis-[benzyl 4,6-(R)-O-benzylidene-2-desoxy-3-O-(2,3,4,5,6-penta-0-sulfo-D-glucit-1-ylcarbamoylmethyl)-α-D-glucopyranosid-2-yl]-terephthalamide decasodium salt. [α]+35.5° (c 0.2; water). MS: m/z 2308 (reconstructed M).

EXAMPLE 14

A. A suspension of 3.0 g of benzyl 6-amino-2-benzyloxycarbonylamino-2,6-didesoxy-α-D-glucopyranoside (see Ex. 9.C.) and 1.33 g of D-gluconic acid g-lactone in 60 ml of dioxan was brought into solution at 80° C. and held at this temperature for a further 18 hours. The separated product was filtered off under suction, washed with dioxan and dried to give D-gluconic acid (benzyl 2-benzyloxycarbonylamino-2,6-didesoxy-α-D-glucopyranosid-6-yl)-amide. [α]+120.0° (c 0.2; dioxan). MS: m/z 603.2 ([M+Na]⁺).

B. A solution of 1.4 g of D-gluconic acid (benzyl 2-benzyloxyarbonylamino-2,6-didesoxy-α-D-glucopyranosid-6-yl)-amide in 5 ml of pyridine was acetylated with 2 ml of acetic anhydride at room temperature for 18 hrs. and concentrated to give 2,3,4,5,6-penta-O-acetyl-D-gluconic acid (benzyl 3,4-di-O-acetyl-2-benzyloxycarbonylamino-2,6-didesoxy-α-D-glucopyranosid-6-yl)-amide. [α]+84.0° (c 0.2; dioxan). MS: m/z 897.3 ([M+Na]⁺).

C. 2,3,4,5,6-Penta-O-acetyl-D-gluconic acid (benzyl 3,4-di-O-acetyl-2-benzyloxycarbonylamino-2,6-didesoxy-α-D-gluco-pyranosid-6-yl)-amide was hydrogenated as described under Ex. 13.B. The reaction product was crystallized from ethyl acetate/ether and gave 2,3,4,5,6-penta-O-acetyl-D-gluconic acid (benzyl 3,4-di-O-acetyl-2-amino-2,6-didesoxy-α-D-glucopyranosid-6-yl)-amide. [α]+96.0° (c 0.2; dioxan). MS: m/z 741.1 ([M+H]⁺).

D. Reaction of 2,3,4,5,6-penta-O-acetyl-D-gluconic acid (benzyl 3,4-di-O-acetyl-2-amino-2,6-didesoxy-α-D-glucopyranosid-6-yl)-amide with 4,4'-biphenyldicarboxylic acid as described in Ex. 9.F. gave biphenyl-4,4'-dicarboxylic acid bis-[[benzyl 3,4-di-O-acetyl- 2,6-didesoxy-6-(2,3,4,5,6-penta-O-acetyl-D-gluconoylamino)-α-D -glucopyranosid-2-yl]-amide]. [α]+123.0° (c 0.2; dioxan). MS: m/z 1687.5 ([M+H]⁺).

E. Biphenyl-4,4'-dicarboxylic acid bis-[[benzyl 3,4-di-O-acetyl-2,6-didesoxy-6-(2,3,4,5,6-penta-O-acetyl-D-gluconoylamino)-α-D -glucopyranosid- 2-yl]-amide] was deacetylated as described in Ex. 1.F. and gave biphenyl-4,4'-dicarboxylic acid bis-[(benzyl 2,6-didesoxy-6-D-gluconoylamino-α-D-glucopyranosid-2-yl)-amide]. MS: m/z 1099.5 ([M+H]⁺).

F. Sulfation of biphenyl-4,4'-dicarboxylic acid bis-[(benzyl 2,6-didesoxy-6-D-gluconoylamino-α-D-glucopyranosid-2-yl)-amide] as described in Ex. 9.H. gave biphenyl-4,4'-dicarboxylic acid bis-[[benzyl 2,6-didesoxy-3,4-di-O-sulfo-6-(2,3,4,5,6-penta-O-sulfo-D-gluconoylamino)-α-D-glucopyranosid-2-yl]-amide] tetradecasodium salt. [α]+73.0° (c 0.2; water). MS: m/z 2527 (reconstructed M).

EXAMPLE 15

A solution of 200 mg of biphenyl-4,4'-dicarboxylic acid bis-[[benzyl 2,6-didesoxy-3,4-di-O-sulfo-6-(2,3,4,5,6-penta-O-sulfo-D-gluconoylamino)-α-D-glucopyranosid-2-yl]-amide] tetradecasodium salt (see Ex. 14.F.) in 12 ml of 2N sodium hydroxide was left at room temperature for 8 hours, neutralized with acidic ion exchanger (Amberlite IR 120 H+) and concentrated. The residue was chromatographed over Sephadex C25 Na⁺) with water and gave biphenyl-4,4'-dicarboxylic acid bis-[[(Z)-benzyl 2,6-didesoxy-3,4-di-O-sulfo-6-(3-desoxy-2,4,5,6-tetra-O-sulfo-D-erythro-hex-2-enonoylamino)-α-D-glucopyranosid-2-yl]-amide] dodecasodium salt. [α]+67.50 (c 0.2; water). MS: m/z 2288 (reconstructed M).

EXAMPLE 16

A. Benzyl 6-amino-2-benzyloxycarbonylamino-2,6-didesoxy-α-D-glucopyranoside (see Ex. 9.C.) and D-ribonic acid g-lactone were reacted as described in Ex. 14.A. and gave D-ribonic acid (benzyl 2-benzyloxycarbonylamino-2,6-didesoxy-α-D-glucopyranosid-6-yl)-amide. [α]+81.5° (c 0.2; dioxan). MS: m/z 551.4 ([M+H]⁺).

B. D-Ribonic acid (benzyl 2-benzyloxycarbonylamino-2,6-didesoxy-α-D-glucopyranosid-6-yl)-amide was acetylated as described in Ex. 14.B. and gave 2,3,4,5-tetra-O-acetyl-D-ribonic acid (benzyl 3,4-di-O-acetyl-2-benzyloxycarbonylamino-2,6-didesoxy-α-D-glucopyranosid-6-yl)-amide. [α]+78.0° (c 0.2; dioxan). MS: m/z 803.2 ([M+H]⁺).

C. 2,3,4,5-Tetra-O-acetyl-D-ribonic acid (benzyl 3,4-di-O-acetyl-2-benzyloxycarbonylamino-2,6-didesoxy-α-D-gluco-pyranosid-6-yl)-amide was hydrogenated as described under Ex. 13.B. and gave 2,3,4,5-tetra-O-acetyl-D-ribonic acid (benzyl 3,4-di-O-acetyl-2-amino-2,6-didesoxy-α-D-glucopyranosid-6-yl)-amide. MS: m/z 669.2 ([M+H]⁺).

D. A suspension of 417 mg of biphenyl-4,4'-dicarboxylic acid in 10 ml of tetrahydrofuran und 10 ml of acetonitrile was treated at room temperature with 0.397 ml of N-methylmorpholine and 604 mg of 2-chloro-2,4- dimethoxy-1,3,5-triazine. After 30 minutes, a solution of 2,3,4,5-tetra-O-acetyl-D-ribonic acid (benzyl 3,4-di-O-acetyl-2-amino-2,6-didesoxy-α-D-gluco-pyranosid-6-yl)-amide in 7.5 ml of tetrahydrofuran and 7.5 ml of acetonitrile was added and the mixture was stirred for 2 hours. Then, insoluble constituents were filtered off and the filtrate was concentrated. There was obtained biphenyl-4,4'-dicarboxylic acid bis-[[benzyl 3,4-di-O-acetyl-2,6-didesoxy-6-(2,3,4,5,6-penta-O-acetyl-D-ribonoylamino)-α-D-glucopyranosid-2-yl]-amide]. [α]+ 127.0° (c 0.2; dioxan). MS: m/z 1562.5 ([M+NH$_4$]$^+$).

E. Biphenyl-4,4'-dicarboxylic acid bis-[[benzyl 3,4-di-O-acetyl-2,6-didesoxy-6-(2,3,4,5,6-penta-O-acetyl-D-ribonoylamino)-α-D -glucopyranosid-2-yl]-amide] was deacetylated as described in Ex. 11.F. and gave biphenyl-4,4'-dicarboxylic acid bis-[(benzyl 2,6-didesoxy-6-D-ribonoylamino-α-D-glucopyranosid-2-yl)-amide]. MS: m/z 1057.2 ([M+Na]$^+$).

F. Sulfation of biphenyl-4,4'-dicarboxylic acid bis-[(benzyl 2,6-didesoxy-6-D-ribonoylamino-α-D-glucopyranosid-2-yl)-amide] as described in Ex. 9.H. gave biphenyl-4,4'-dicarboxylic acid bis-[[benzyl 2,6-didesoxy-3,4-di-O-sulfo-6-(2,3,4,5-tetra-O-sulfo-D-ribonoylamino)-α-D-glucopyranosid-2-yl]-amide] dodecasodium salt. [α]+ 91.00 (c 0.2; water). MS: m/z 2264 (reconstructed M).

EXAMPLE 17

A. Benzyl 6-amino-2-benzyloxycarbonylamino-2,6-didesoxy-α-D-glucopyranoside (see Ex. 9.C.) and 2-(R)-hydroxy-3,3-dimethyl-g-butyrolactone were reacted as described in Ex. 14.A. After addition of 30% of the lactone, the mixture was stirred for 1 day at 80° C. and the crude product was acetylated as described in Ex. 14.B. to give (R)-2,4-diacetoxy-3,3-dimethyl-butyric acid (benzyl 3,4-di-O-acetyl-2-benzyloxycarbonylamino-2,6-didesoxy-α-D-glucopyranosid-6-yl)-amide. [α]+99.0° (c 0.2; dioxan). MS: m/z 701.2 ([M+H]$^+$).

B. (R)-2,4-Diacetoxy-3,3-dimethyl-butyric acid (benzyl 3,4-di-O-acetyl-2-benzyloxycarbonylamino-2,6-didesoxy-α-D-gluco-pyranosid-6-yl)-amide was hydrogenated as described under Ex. 13.B. and gave (R)-2,4-diacetoxy-3,3-dimethyl-butyric acid (benzyl 3,4-di-O-acetyl-2-amino-2,6-didesoxy-α-D-gluco-pyranosid-6-yl)-amide. MS: m/z 657.5 ([M+H]$^+$).

C. Reaction of (R)-2,4-diacetoxy-3,3-dimethyl-butyric acid (benzyl 3,4-di-O-acetyl-2-amino-2,6-didesoxy-α-D-gluco-pyranosid-6-yl)-amide with biphenyl-4,4'-dicarboxylic acid as described in Ex. 16. D. gave biphenyl-4,4'-dicarboxylic acid bis-[[benzyl 3,4-di-O-acetyl-6-((R)-2,4-diacetoxy-3,3-dimethyl-butyrylamino)-2,6-didesoxy-α-D-glucopyranosid-2-yl]-amide]. [α]+ 140.0° (c 0,2; dioxan). MS: m/z 1361.5 ([M+Na]$^+$).

D. Biphenyl-4,4'-dicarboxylic acid bis-[[benzyl 3,4-di-O-acetyl-6-((R)-2,4-diacetoxy-3,3-dimethyl-butyrylamino)-2,6-didesoxy-α-D-glucopyranosid-2-yl]-amide] was deacetylated as described in Ex. 11.F. and gave biphenyl-4,4'-dicarboxylic acid bis-[[benzyl 2,6-didesoxy-6-((R)-2,4-dihydroxy-3,3-dimethyl-butyrylamino)-α-D-glucopyranosid-2-yl]-amide]. [α]+119.0° (c 0.2; dioxan). MS: m/z 1025.8 ([M+Na]$^+$).

E. Sulfation of biphenyl-4,4'-dicarboxylic acid bis-[[benzyl 2,6-didesoxy-6-((R)-2,4-dihydroxy-3,3-dimethyl-butyrylamino)-α-D -glucopyranosid-2-yl]-amide] as described in Ex. 9.H. gave biphenyl-4,4'-dicarboxylic acid bis-[[benzyl 2,6-didesoxy-3,4-di-O-sulfo-6-((R)-2,4-bis-hydroxysulfonyloxy-3,3-dimethyl-butyrylamino)-α-D-glucopyranosid-2-yl]-amide] octasodium salt. [α]+ 106.5° (c 0.2; water). MS: m/z 1820 (reconstructed M).

EXAMPLE 18

A. Benzyl 6-amino-2-benzyloxycarbonylamino-2,6-didesoxy-α-D-glucopyranoside (see Ex. 9.C.) and (S)-hydroxymethyl-g-butyrolactone were reacted as described in Ex. 14.A. After the addition of 30% of the lactone, the mixture was stirred for 1 day at 80° C. and the crude product was crystallised from ethyl acetate/methylene chloride to give (S)-4,5-dihydroxy-pentanoic acid (benzyl 2-benzyloxycarbonylamino-2,6-didesoxy-α-D-gluco-pyranosid-6-yl)-amide. [α]+73.0° (c 0.2; dioxan). MS: m/z 519.5([M+H]$^+$).

B. (S)-4,5-Dihydroxy-pentanoic acid (benzyl 2-benzyloxycarbonylamino-2,6-didesoxy-α-D-glucopyranosid-6-yl)-amide was acetylated as described in Ex. 14.B. and gave (S)-4,5-diacetoxy-pentanoic acid (benzyl 3,4-di-O-acetyl-2-benzyloxy-carbonylamino-2,6-didesoxy-α-D-glucopyranosid-6-yl)-amide. [α]+89.5° (c 0.2; dioxan). MS: m/z 687.2 ([M+H]$^+$).

C. (S)-4,5-Diacetoxy-pentanoic acid (benzyl 3,4-di-O-acetyl-2-benzyloxycarbonylamino-2,6-didesoxy-α-D-glucopyranosid-6-yl)-amide was hydrogenated as described under Ex. 13.B. and gave (S)-4,5-diacetoxy-pentanoic acid (benzyl 3,4-di-O-acetyl-2-amino-2,6-didesoxy-α-D-glucopyranosid-6-yl)-amide. MS: ml/z 553.4 ([M+H]$^+$)

D. Reaction of (S)-4,5-diacetoxy-pentanoic acid (benzyl 3,4-di-O-acetyl-2-amino-2,6-didesoxy-α-D-glucopyranosid-6-yl)-amide with biphenyl-4,4'-dicarboxylic acid as described in Ex. 16.D. gave biphenyl-4,4'-dicarboxylic acid bis-[[benzyl 3,4-di-O-acetyl-6-[(S)-4,5-diacetoxy-pentanoylamino]-2,6-didesoxy-α-D-glucopyranosid-2-yl]-amide]. [α]+132.0° (c 0.2; dioxan). MS: m/z 1361.5 ([M+Na]$^+$).

E. Biphenyl-4,4'-dicarboxylic acid bis-[[benzyl 3,4-di-O-acetyl-6-[(S)-4,5-diacetoxy-pentanoylamino]-2,6-didesoxy-α-D-glucopyranosid-2-yl]-amide] was deacetylated as described in Ex. 11.F. and gave biphenyl-4,4'-dicarboxylic acid bis-[[benzyl 2,6-didesoxy-6-[(S)-4,5-dihydroxy-pentanoylamino]-α-D-gluco-pyranosid-2-yl]-amide]. [α]+92.00 (c 0.2; dioxan). MS: m/z 997.9 ([M+Na]$^+$).

F. Sulfation of biphenyl-4,4'-dicarboxylic acid bis-[[benzyl 2,6-didesoxy-6-[(S)-4,5-dihydroxy-pentanoylamino]-α-D-glucopyranosid-2-yl]-amide] as described in Ex. 9.H. gave biphenyl-4,4'-dicarboxylic acid bis-[[benzyl 2,6-didesoxy-6-[(S)-4,5-bis-hydroxysulfonyloxy-pentanoylamino]-3,4-di-O-sulfo-α-D-glucopyranosid-2-yl]-amide] octasodium salt. [α]+93.5° (c 0.2; water). MS: m/z 1792 (reconstructed M).

EXAMPLE 19

A. Reaction of 2,3,4,5,6-penta-O-acetyl-D-gluconic acid (benzyl 3,4-di-O-acetyl-2-amino-2,6-didesoxy-α-D-glucopyranosid-6-yl)-amide (see Ex. 14.C.) with terephthalic acid as described in Ex. 16.D. gave terephthalic acid bis-[[benzyl 3,4-di-O-acetyl-2,6-didesoxy-6-(2,3,4,5,6-penta-O-acetyl-D-gluconoylamino)-α-D-glucopyranosid-2-yl]-amide]. [α]+96.5° (c 0.2; chloroform). MS: m/z 1611.5 ([M+H]$^+$).

B. A solution of terephthalic acid bis-[[benzyl 3,4-di-O-acetyl-2,6-didesoxy-6-(2,3 ,4,5,6-penta-O-acetyl-D-gluconoylamino)-α-D-glucopyranosid-2-yl]-amide] in methanol/dioxan 2:1 was deacetylated as described in Ex. 11.F. and gave terephthalic acid bis-[(benzyl 2,6-didesoxy-6-D-gluconoylamino-α-D-glucopyranosid-2-yl)-amide]. MS: m/z 1023.3 ([M+H]$^+$).

C. Sulfation of terephthalic acid bis-[(benzyl 2,6-didesoxy-6-D-gluconoylamino-α-D-glucopyranosid-2-yl)-amide]

as described in Ex. 9.H. gave terephthalic acid bis-[[benzyl 2,6-didesoxy-3,4-di-O-sulfo-6-(2,3,4,5,6-penta-O-sulfo-D-gluconoylamino)-α-D-glucopyranosid-2-yl]-amide] tetradecasodium salt, [α]+79.5° (c 0.2; water), MS: m/z 2452 (reconstructed M).

EXAMPLE 20

A. Reaction of 2,3,4,5,6-penta-O-acetyl-D-gluconic acid (benzyl 3,4-di-O-acetyl-2-amino-2,6-didesoxy-α-D-glucopyranosid-6-yl)-amide (see Ex. 14.C.) with diphenylmethane-4,4'-dicarboxylic acid in dimethylformamide gave, as described in Ex. 16.D., diphenylmethane-4,4'-dicarboxylic acid bis-[[benzyl 3,4-di-O-acetyl-6-(2,3,4,5,6-penta-O-acetyl-D-gluconoylamino)-2,6-didesoxy-α-D-glucopyranosid-2-yl]-amide], [α]+100.0° (c 0.2; dioxan), MS: m/z 1719.0 ([α+NH$_4$]$^+$).

B. Diphenylmethane-4,4'-dicarboxylic acid bis-[[benzyl 3,4-di-O-acetyl-6-(2,3,4,5,6-penta-O-acetyl-D-gluconoylamino)-2,6-didesoxy-α-D-glucopyranosid-2-yl]-amide] was deacetylated as described in Ex. 11.F. and gave diphenylmethane-4,4'-dicarboxylic acid bis-[(benzyl 2,6-didesoxy-6-D-gluconoylamino-α-D-glucopyranosid-2-yl)-amide], MS: m/z 1113 ([M+H]$^+$).

C. Sulfation of diphenylmethane-4,4'-dicarboxylic acid bis-[(benzyl $^2$,$^6$-didesoxy-6-D-gluconoylamino-α-D-glucopyranosid-2-yl)-amide] as described in Ex. 9.H. gave diphenylmethane-4,4'-dicarboxylic acid bis-[[benzyl 2,6-didesoxy-6-(2,3,4,5,6-penta-O-sulfo-D-gluconoylamino)-3,4-di-O-sulfo-α-D-glucopyranosid-2-yl]-amide] tetradecasodium salt, [α]+66.5° (c 0.2; water), MS: m/z 2542 (reconstructed M).

EXAMPLE 21

A. Reaction of 2,3,4,5,6-penta-O-acetyl-D-gluconic acid (benzyl 3,4-di-O-acetyl-2-amino-2, 6-didesoxy-α-D-glucopyranosid-6-yl)-amide (see Ex. 14.C.) with naphthalene-2,6-dicarboxylic acid in dimethylformamide gave, as described in Ex. 16.D., naphthalene-2,6-dicarboxylic acid bis-[[benzyl 3,4-di-O-acetyl-6-(2,3,4,5,6-penta-O-acetyl-D-gluconoylamino)-2,6-didesoxy-α-D-glucopyranosid-2-yl]-amide], [α]+1 17.5° (c 0.2; dioxan), MS: m/z 1685.5 ([M+Na]$^+$).

B. Naphthalene-2,6-dicarboxylic acid bis-[[benzyl 3,4-di-O-acetyl-6-(2,3,4,5,6-penta-O-acetyl-D-gluconoylamino)-2,6-didesoxy-α-D-glucopyranosid-2-yl]-amide] was deacetylated as described in Ex. 11.F. and gave naphthalene-2,6-dicarboxylic acid bis-[(benzyl 2,6-didesoxy-6-D-gluconoylamino-α-D-gluco-pyranosid-2-yl)-amide], MS: m/z 1095.8 ([M+Na]$^+$).

C. Sulfation of naphthalene-2,6-dicarboxylic acid bis-[(benzyl 1 5 2,6-didesoxy-6-D-gluconoylamino-α-D-glucopyranosid-2-yl)-amide] as described in Ex. 9.H. gave naphthalene-2,6-dicarboxylic acid bis-[[benzyl 2,6-didesoxy-6-(2,3,4,5,6-penta-O-sulfo-D-gluconoylamino)-3,4-di-O-sulfo-α-D-glucopyranosid-2-yl]-amide] tetradecasodium salt, [ac]+76.5° (c 0.2; water), MS: m/z 2501 (reconstructed M).

EXAMPLE 22

A. Benzyl 6-amino-2-benzyloxycarbonylamino-2,6-didesoxy-α-D-glucopyranoside (see Ex. 9.C.) and D-glucoheptono-1,4-lactone were reacted with one another as described in Ex. 14.A. The reaction product was acetylated as described in Ex. 14.B. and gave 2,3,4,5,6,7-hexa-O-acetyl-D-glycero-D-guloheptanoic acid (benzyl 3,4-di-O-acetyl-2-benzyloxycarbonylamino-2,6-didesoxy-α-D-glucopyranosid-6-yl)-amide, [α]+83.0° (c 0.2; dioxan), MS: m/z 969 ([M+Na]$^+$).

B. 2,3,4,5,6,7-Hexa-O-acetyl-D-glycero-D-guloheptanoic acid (benzyl 3,4-di-O-acetyl-2-benzyloxycarbonylamino-2,6-didesoxy-α-D-glucopyranosid-6-yl)-amide was hydrogenated as described under Ex. 13.B. and gave 2,3,4,5,6,7-hexa-O-acetyl-D-glycero-D-guloheptanoic acid (benzyl 3,4-di-O-acetyl-2-amino- 2,6-didesoxy-α-D-glucopyranosid-6-yl)-amide, [α]+92.0° (c 0.2; dioxan), MS: m/z 813.3 ([M+H]$^+$).

C. Reaction of 2,3,4,5,6,7-hexa-O-acetyl-D-glycero-D-guloheptanoic acid (benzyl 3,4-di-O-acetyl-2-amino-2,6-didesoxy-α-D-glucopyranosid-6-yl)-amide with naphthalene-2,6-dicarboxylic acid in dimethylformamide as described in Ex. 16.D. gave naphthalene-2,6-dicarboxylic acid bis-[[benzyl 3,4-di-O-acetyl-2,6-didesoxy-6-(2,3,4,5,6,7-hexa-O-acetyl-D-glycero-D-gulo-heptanoylamino)-α-D-glucopyranosid-6-yl]-amide], [α]+110.50 (c 0.2; dioxan), MS: m/z 1827.4 ([M+Na]$^+$).

D. Naphthalene-2,6-dicarboxylic acid bis-[[benzyl 3,4-di-O-acetyl-2,6-didesoxy-6-(2,3,4,5,6,7-hexa-O-acetyl-D-glycero-D-gulo-heptanoylamino)-α-D-glucopyranosid-6-yl]-amide] was deacetylated as described in Ex. 1.F. and gave naphthalene-2,6-dicarboxylic acid bis-[[benzyl 2,6-didesoxy-6-(D-glycero-D-gulo-heptanoylamino)-α-D-glucopyranosid-6-yl]-amide], MS: m/z 1157.1 ([M+Na]$^+$).

E. Sulfation of naphthalene-2,6-dicarboxylic acid bis-[[benzyl 2,6-didesoxy-6-(D-glycero-D-gulo-heptanoylamino)-α-D-glucopyranosid-6-yl]-amide] as described in Ex. 9.H. gave naphthalene-2,6-dicarboxylic acid bis-[[benzyl 2,6-didesoxy-3,4-di-O-sulfo-6-(2,3,4,5,6,7-hexa-O-sulfo-D-glycero-D-gulo-heptan-oylamino)-α-D-glucopyranosid-6-yl]-amide] hexadecasodium salt, [α]+54.5° (c 0.2; water), MS: ml/z 2765 (reconstructed M).

EXAMPLE 23

A. Reaction of 2,3,4,5,6-penta-O-acetyl-D-gluconic acid (benzyl 3,4-di-O-acetyl-2-amino-2,6-didesoxy-α-D-glucopyranosid-6-yl)-amide (see Ex. 14.C.) with (Z)-stilbene-4,4'-dicarboxylic acid in dimethylformamide gave, as described in Ex. 16.D., (Z)-4,4'-stilbene-4,4'-dicarboxylic acid bis-[[benzyl 3,4-di-O-acetyl-6-(2,3,4,5,6-penta-O-acetyl-D-gluconoylamino)-2,6-didesoxy-α-D-glucopyranosid-2-yl]-amide], [α]+105.5° (c 0.2; dioxan), MS: m/z 1736.2 ([M+Na]$^+$).

B. (Z)-4,4'-Stilbene-4,4'-dicarboxylic acid bis-[[benzyl 3,4-di-O-acetyl-6-(2,3,4,5,6-penta-O-acetyl-D-gluconoylamino)-2,6-didesoxy-α-D-glucopyranosid-2-yl]-amide] was deacetylated as described in Ex. 11.F. and gave (Z)-stilbene-4,4'-dicarboxylic acid bis-[(benzyl 2,6-didesoxy-6-D-gluconoylamino-α-D-glucopyranosid-2-yl)-amide], MS: m/z 1148.6 ([M+Na]$^+$).

C. Sulfation of (Z)-stilbene-4,4'-dicarboxylic acid bis-[(benzyl 1 0 2,6-didesoxy-6-D-gluconoylamino-α-D-glucopyranosid-2-yl)-amide] as described in Ex. 9.H. gave (Z)-stilbene-4,4'-dicarboxylic acid bis-[[benzyl 2,6-didesoxy-6-(2,3,4,5,6-penta-O-sulfo-D-gluconoylamino)-3,4-di-O-sulfo-α-D-glucopyranosid-2-yl]-amide] tetradecasodium salt, [α]+72.5° (c 0.2; water), MS: m/z 2553 (reconstructed M).

EXAMPLE 24

A. Reaction of 2,3,4,5,6-penta-O-acetyl-D-gluconic acid (benzyl 3,4-di-O-acetyl-2-amino-2,6-didesoxy-α-D- glucopyranosid-6-yl)-amide (see Ex. 14.C.) with isophthalic acid gave, as described in Ex. 16.D., isophthalic acid bis-[[benzyl 3,4-di-O-acetyl-6-(2,3,4,5,6- penta-O-acetyl-D-gluconoylamino)-2,6-didesoxy-α-D-glucopyranosid-2-yl]-amide], [α]+105.0° (c 0.2; dioxan), MS: m/z 1612.0 ([M+H]⁺).

B. Isophthalic acid bis-[[benzyl 3,4-di-O-acetyl-6-(2,3,4,5,6-penta-O-acetyl-D-gluconoylamino)-2,6-didesoxy-α-D-glucopyranosid-2-yl]-amide] was deacetylated as described in Ex. 11.F. and gave isophthalic acid bis-[(benzyl 2,6-didesoxy-6-D-glucon-oylamino-α-D-glucopyranosid-2-yl)-amide], MS: m/z 1023.4 ([M+H]⁺)

C. Sulfation of isophthalic acid bis-[(benzyl 2,6-didesoxy-6-D-gluconoylamino-α-D-glucopyranosid-2-yl)-amide] as described in Ex. 9.H. gave isophthalic acid bis-[[benzyl 2,6-didesoxy-6-(2,3,4,5,6-penta-O-sulfo-D-gluconoylamino)-3,4-di-O-sulfo-α-D-glucopyranosid-2-yl]-amide] tetradecasodium salt, [α]+74.0° (c 0.2; water), MS: m/z 2451 (reconstructed M).

EXAMPLE 25

A. Benzyl 6-amino-2-benzyloxycarbonylamino-2,6-didesoxy-α-D-glucopyranoside (see Ex. 9.C.) and D-gulonic acid g-lactone were reacted as described in Ex. 14.A. The crude product was acetylated as described in Ex. 14.B. and gave 2,3,4,5,6-penta-O-acetyl-D-ulonic acid (benzyl 3,4-di-O-acetyl-2-benzyloxycarbonylamino-2,6-didesoxy-α-D-glucopyranosid-6-yl)-amide, [α]+88.0° (c 0.2; dioxan), MS: m/z 897.4 ([M+Na]⁺).

B. 2,3,4,5,6-Penta-O-acetyl-D-gulonic acid (benzyl 3,4-di-O-acetyl-2-benzyloxycarbonylamino-2,6-didesoxy-α-D-glucopyranosid-6-yl)-amide was hydrogenated as described under Ex. 13.B. and gave 2,3,4,5,6-penta-O-acetyl-D-gulonic acid (benzyl 3,4-di-O-acetyl-2-amino-2,6-didesoxy-α-D-glucopyranosid-6-yl)-amide, [α]+95.0° (c 0.2; dioxan), MS: m/z 741.4 ([M+H]⁺).

C. Reaction of 2,3,4,5,6-penta-O-acetyl-D-gulonic acid (benzyl 3,4-di-O-acetyl-2-amino-2,6-didesoxy-α-D-glucopyranosid-6-yl)-amide with isophthalic acid gave, as described in Ex. 16.D., isophthalic acid bis-[[benzyl 3,4-di-O-acetyl-6-(2,3,4,5,6-penta-O-acetyl-D-gulonoylamino)-2,6-didesoxy-α-D-glucopyranosid-2-yl]-amide], [α]+102.0° (c 0.2; dioxan), MS: m/z 1633.1 ([M+Na]⁺).

D. Isophthalic acid acid bis-[[benzyl 3,4-di-O-acetyl-6-(2,3,4,5, 6-penta-O-acetyl-D-gulonoylamino)-2,6-didesoxy-α-D-glucopyranosid-2-yl]-amide] was deacetylated as described in Ex. 11.F. and gave isophthalic acid bis-[(benzyl 2,6-didesoxy-6-D-gulonoylamino-α-D-glucopyranosid-2-yl)-amide], MS: m/z 1045.6 ([M+Na]⁺).

E. Sulfation of isophthalic acid acid bis-[(benzyl 2,6-didesoxy-6-D-gulonoylamino-α-D-glucopyranosid-2-yl)-amide] as described in Ex. 9.H. gave isophthalic acid acid bis-[[benzyl 2,6-didesoxy-6-(2,3,4,5,6-penta-O-sulfo-D-gulonoylamino)-3,4-di-O-sulfo-α-D-glucopyranosid- 2-yl]-amide] tetradecasodium salt, [α]+90.5° (c 0.2; water), MS: m/z 2452 (reconstructed M).

EXAMPLE 26

A. Benzyl 6-amino-2-benzyloxycarbonylamino-2,6-didesoxy-α-glucopyranoside (see Ex. 9.C.) and L-gulonic acid g-lactone were reacted as described in Ex. 14.A. The crude product was acetylated as described in Ex. 14.B. and gave 2,3,4,5,6-penta-O-acetyl-L-gulonic acid (benzyl 3,4-di-O-acetyl-2-benzyloxy-carbonylamino-2,6-didesoxy-α-D-glucopyranosid-6-yl)-amide, [α]+71.0° (c 0.2; dioxan), MS: m/z 875.2 ([M+H]⁺).

B. 2,3,4,5,6-Penta-O-acetyl-L-gulonic acid (benzyl 3,4-di-O-acetyl-2-benzyloxycarbonylamino-2,6-didesoxy-α-D-glucopyranosid-6-yl)-amide was hydrogenated as described under Ex. 13.B. and gave 2,3,4,5,6-penta-O-acetyl-L-gulonic acid (benzyl 3,4-di-O-acetyl-2-amino-2,6-didesoxy-α-D-glucopyranosid-6-yl)-amide, [α]+75.50 (c 0.2; dioxan), MS: m/z 763.6 ([M+Na]⁺).

C. Reaction of 2,3,4,5,6-penta-O-acetyl-L-gulonic acid (benzyl 3,4-di-O-acetyl-2-amino-2,6-didesoxy-α-D-glucopyranosid-6-yl)-amide with isophthalic acid acid gave, as described in Ex. 16.D., isophthalic acid acid bis-[[benzyl 3,4-di-O-acetyl-6-(2,3,4,5,6-penta-O-acetyl-L-gulonoylamino)-2,6-didesoxy-α-D-glucopyranosid-2-yl]-amide], [α]+91.5° (c 0.2; dioxan), MS: m/z 1630.0 ([M+NH₄]⁺).

D. Isophthalic acid acid bis-[[benzyl 3,4-di-O-acetyl-6-(2,3,4,5,6-penta-O-acetyl-L-gulonoylamino)-2,6-didesoxy-α-D-glucopyranosid-2-yl]-amide] was deacetylated as described in Ex. 11.F. and gave isophthalic acid acid bis-[(benzyl 2,6-didesoxy-6-L-gulonoylamino-α-D-glucopyranosid-2-yl)-amide], MS: m/z 1045.9 ([M+Na]⁺).

E. Sulfation of isophthalic acid acid bis-[(benzyl 2,6-didesoxy-6-L-gulonoylamino-α-D-glucopyranosid-2-yl)-amide] as described in Ex. 9.H. gave isophthalic acid acid bis-[[benzyl 2,6-didesoxy- 6-(2,3,4,5,6-penta-O-sulfo-L-gulonoylamino)-3,4-di-O-sulfo-α-D-glucopyranosid-2-yl]-amide] tetradecasodium salt, [α]+52.5° (c 0.2; water), MS: m/z 2431 (reconstructed M−Na).

EXAMPLE 27

A. Reaction of 2,3,4,5,6,7-hexa-O-acetyl-D-glycerα-guloheptanoic acid (benzyl 3,4-di-O-acetyl-2-amino-2,6-didesoxy-α-D-glucopyranosid-6-yl)-amide (see Ex. 22.B.) with isophthalic acid in dimethylformamide as described in Ex. 16.D. gave isophthalic acid bis-[[benzyl 3,4-di-O-acetyl-6-(2,3,4,5,6,7-hexa-O-acetyl-D-glycero-D-gulo-heptanoylamino)-2,6-didesoxy-α-D-glucopyranosid-6-yl]-amide], [α]+99.0° (c 0.2; dioxan), MS: m/z 1773.0 ([M+NH₄]⁺).

B. Isophthalic acid bis-[[benzyl 3,4-di-O-acetyl-6-(2,3,4,5, 6,7-hexa-O-acetyl-D-glycer α-gulo-heptanoylamino)-2, 6-didesoxy-x-D-glucopyranosid-6-yl]-amide] was deacetylated as described in Ex. 11.F. and gave isophthalic acid bis-[[benzyl 2,6-didesoxy-6-(D-glycer-D-gulo-heptanoylamino)-α-D-glucopyranosid-6-yl]-amide], MS: m/z 1083.2 ([M+H]⁺).

C. Sulfation of isophthalic acid bis-[[benzyl 2,6-didesoxy-6-D-glycer-D-gulo-heptanoylamino)-α-D-glucopyranosid-6-yl]-amide] as described in Ex. 9.H. gave isophthalic acid bis-[[benzyl 2,6-didesoxy-6-(2,3,4, 5,6,7-hexa-O-sulfα-glycer-D-gulo-heptanoylamino)-3,4-di-O-sulfo-α-D-glucopyranosid-6-yl]-amide] hexadecasodium salt, [α]+71.0° (c 0.2; water), MS: m/z 2715 (reconstructed M).

EXAMPLE 28

A. Benzyl 6-amino-2-benzyloxycarbonylamino-2,6-didesoxy-α-D-glucopyranoside (see Ex. 9.C.) was reacted with isophthalic acid in dimethylformamide as described in Ex. 16.D. The crude product was acetylated as described in Ex. 14.B. and gave isophthalic acid bis-(benzyl 3,4-di-O-acetyl-2-benzyloxycarbonylamino-2,6-didesoxy-α-D-glucopyranosid-6-yl)-amide, [α]+101.5° (c 0.2; dioxan), MS: m/z 1125.5 ([M+Na]⁺).

B. Isophthalic acid bis-(benzyl 3,4-di-O-acetyl-2-benzyloxy-carbonylamino-2,6-didesoxy-α-D-glucopyranosid-6-yl)-amide was hydrogenated as described under Ex. 13.B. and gave isophthalic acid bis-(benzyl 3,4-di-O-acetyl-2-amino-2,6-didesoxy- α-D-glucopyranosid-6-yl)-amide. [α]+92.0° (c 0.2; dioxan). MS: m/z 813.3 ([M+H]$^+$).

C. Isophthalic acid bis-(benzyl 3,4-di-O-acetyl-2-amino-2,6-didesoxy-α-D-glucopyranosid-6-yl)-amide and D-gluconic acid glactone were reacted as described in Ex. 14.A. The crude product was acetylated as described in Ex. 14.B. and gave isophthalic acid bis-[benzyl 3,4-di-O-acetyl-2,6-didesoxy-2-(2,3,4,5,6-penta-O-acetyl-D-gluconoylamino)-α-D-glucopyranosid-6-yl]-amide. [α]+69.40 (c 0.2; dioxan). MS: m/z 1633.6 ([M+Na]$^+$).

D. Isophthalic acid bis-[benzyl 3,4-di-O-acetyl-2,6-didesoxy-2-(2,3,4,5,6-penta-O-acetyl-D-gluconoylamino)-α-D-glucopyranosid-6-yl]-amide was deacetylated as described in Ex. 11.F. and gave isophthalic acid bis-(benzyl 2,6-didesoxy-2-D-gluconoylamino-α-D-glucopyranosid-6-yl)-amide. MS: m/z 1046.8 ([M+Na]$^+$).

E. Sulfation of isophthalic acid bis-(benzyl 2,6-didesoxy-2-D-gluconoylamino-α-D-glucopyranosid-6-yl)-amide as described in Ex. 9.H. gave isophthalic acid bis-[benzyl 2,6-didesoxy-3,4-di-O-sulfo-2-(2,3,4,5,6-penta-O-sulfo-gluconoylamino)-α-D-glucopyranosid-6-yl]-amide tetradecasodium salt. [α]+45.0° (c 0.2; water). MS: m/z 2451 (reconstructed M).

EXAMPLE 29

A. Benzyl 6-amino-2-benzyloxycarbonylamino-2,6-didesoxy-α-D-glucopyranoside (see Ex. 9.C.) was reacted with diphenylmethane-4,4'-dicarboxylic acid in dimethylformamide as described in Ex. 16.D. and gave diphenylmethane-4,4'-dicarboxylic acid bis-[(benzyl 2-benzyloxycarbonylamino-2,6-didesoxy-α-D-glucopyranosid- 6-yl)-amide]. [α]+82.2° (c 0.2; dioxan). MS: m/z 1047.6 ([M+Na]$^+$).

B. Diphenylmethane-4,4'-dicarboxylic acid bis-[(benzyl-2-benzyloxycarbonylamino-2,6-didesoxy-α-D-glucopyranosid-6-yl)-amide] was hydrogenated as described under Ex. 13.B. and gave diphenylmethane-4,4'-dicarboxylic acid-bis-[(benzyl 2-amino-2,6-didesoxy-α-D-glucopyranosid-6-yl)-amide] which was used in the next step (Example 29.D.) without further purification.

C. A solution of 7.4 g of 4-fluoro-3-nitro-benzoic acid in 100 ml of dimethylformamide was treated with 16.0 g of D-glucamine and stirred at room temperature for 4 hours. After the addition of 6 ml of triethylamine, the mixture was stirred at 40° C. for a further 16 hours. The reaction solution was evaporated. The residue was stirred at room temperature with 400 ml of pyridine and 200 ml of acetic anhydride for 5hours. After concentration, the residue obtained was treated with water and acidified to pH 2–3 with 5% hydrochloric acid solution and extracted with ethyl acetate. The organic extracts were washed with ice-water and saturated sodium chloride solution, dried over magnesium sulfate and evaporated. The residue was chromatographed over silica gel with ethyl acetate. The product fractions were concentrated and the residue was crystallized from ether to give 4-(2,3,4, 5,6-penta-O-acetyl-D-glucit-1-ylamino)-3-nitrobenzoic acid as yellow crystals. [α]−23.0° (c 0.5; DMSO). MS: m/z 579.7 ([M+Na]$^+$).

D. Diphenylmethane-4,4'-dicarboxylic acid bis-[(benzyl 2-amino-2,6-didesoxy-α-D-glucopyranosid-6-yl)-amide] was reacted with 4-(2,3,4,5,6-penta-O-acetyl-D-glucit-1-ylamino)-3-nitrobenzoic acid in dimethylformamide as described in Ex. 16.D. and gave diphenylmethane-4,4'-dicarboxylic acid bis-[[benzyl 2,6-didesoxy-2-[4-(2,3,4,5,6-penta-O-acetyl-D-glucit-1-ylamino)-3-nitro-benzoylamino]-α-D-glucopyranosid-6-yl]-amide]. [α]+21.4° (c 0.5; dimethyl sulfoxide). MS: m/z 1856.3 ([M+Na]$^+$).

E. Diphenylmethane-4,4'-dicarboxylic acid bis-[[benzyl 2,6-di-desoxy-2-[4-(2,3,4,5,6-penta-O-acetyl-D-glucit-1-ylamino)-3-nitro-benzoylamino]-α-D-glucopyranosid-6-yl]-amide] was acetylated as described in Ex. 14.B. The crude product was chromatographed over silica gel with methylene chloride/isopropanol and gave diphenylmethane-4,4'-dicarboxylic acid bis-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide]. [α]+61.4° (c 0.5; chloroform). MS: m/z 2025.6 ([M+Na]$^+$).

F. Diphenylmethane-4,4'-dicarboxylic acid bis-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide] was deacetylated as described in Ex. 11.F. and gave diphenylmethane-4,4'-dicarboxylic acid bis-[[benzyl 2,6-didesoxy-2-(4-D-glucit-1-ylamino-3-nitro-benzoylamino)-α-D-glucopyranosid-6-yl]-amide]. [α]+53.4° (c 0.5; DMSO). MS: m/z 1436.4 ([M+Na]$^+$).

G. A suspension of 0.94 g of diphenylmethane-4,4'-dicarboxylic acid bis-[[benzyl 2,6-didesoxy-2-(4-D-glucit-1-ylamino-3-nitro-benzoylamino)-α-D-glucopyranosid-6-yl]-amide] and 3.85 g of sulfur trioxide-triethylamine complex in 15 ml of absolute dimethylformamide was stirred at 45° C. for 20 hours. After cooling, the mixture was concentrated in a high vacuum. The residue was treated with a solution of 3.26 g of sodium acetate in 50 ml of water and evaporated, and the residue was treated several times with water and evaporated each time. The thus- obtained residue was taken up in water and chromatographed on Sephadex® LH20 and SP Sephadex® C-25. The product fractions were lyophilized and gave diphenylmethane-4,4'-dicarboxylic acid bis-[[benzyl-2,6-didesoxy-2-[4-(2,3,4,5,6-penta-O-sulfo-glucit-1-ylamino)-3-nitro-benzoylamino]-3,4-di-O-sulfo-α-D-glucopyranosid-6-yl]-amide] tetradecasodium salt. [α]+64.0° (c 0.4; water). MS: m/z 2842.0 (reconstructed M).

EXAMPLE 30

A. 8.78 g of 2-chloro-2,4-dimethoxy-1,3,5-triazine were added at 0° C. to a solution of 27.8 g of 4-(2,3,4,5,6-penta-O-acetyl-D-glucit-1-ylamino)-3-nitro-benzoic acid (see Ex. 29.C.) and 5.32 g of N-methylmorpholine in 150 ml of absolute dimethylformamide. The reaction mixture was stirred at this temperature for 2 hours and then treated with 14.0 g of benzyl 2-amino-2-desoxy-α-D-glucopyranoside (Meyer zu Reckendorf, Chem. Ber. 107, 869 (1974)). The mixture was stirred for a further 18 hours and then concentrated in a vacuum. The residual syrup was purified by chromatography on silica gel with methylene chloride/isopropanol and gave benzyl 2-desoxy-2-[3-nitro-4-(2,3,4,5,6-penta-O-acetyl-D-glucit-1-ylamino)-benzoylamino]-α-D-glucopyranoside. [α]+33.6° (c 0.5; DMSO). MS: m/z 808.4 ([M+H]$^+$).

B. 10.9 g of p-toluenesulfonyl chloride were added in portions to a solution of 30.0 g of benzyl 2-desoxy-2-[3-nitro-4-(2,3,4,5,6-penta-O-acetyl-D-glucit-1-ylamino)- benzoylamino]-α-D-glucopyranoside in 250 ml of absolute pyridine. After completion of the addition the reaction mixture was stirred at room temperature for 7 hours and then concentrated. The residue was taken up in ethyl acetate and extracted with water. The organic phases were washed with dilute sulfuric acid, water and saturated sodium chloride solution, dried over magnesium sulfate and evaporated. The residue was chromatographed on silica gel with methylene chloride/isopropanol and gave benzyl 2-desoxy-2-[3-nitro-4-(2,3,4,5,6-penta-O-acetyl-D-glucit 1-ylamino)-benzoylamino]-6-O-(p-tolylsulfonyl)-α-D-glucopyranoside, $[\alpha]+31.4°$ (c 0.5; DMSO), MS: m/z 984.7 ([M+K]$^+$).

C. 6.5 g of sodium azide were added to a solution of 31.0 g of benzyl 2-desoxy-2-[3-nitro-4-(2,3,4,5,6-penta-O-acetyl-D-glucit-1-ylamino)-benzoylamino]-6-O-(p-tolylsulfonyl)-α-D-glucopyranoside in 250 ml of absolute dimethylformamide. The reaction mixture was stirred at 65° C. for 6 hours and then concentrated. The residue was poured into ice-water and extracted with ethyl acetate. The organic phases were washed with water and saturated sodium chloride solution, dried over magnesium sulfate and evaporated. The residue was chromatographed on silica gel with methylene chloride/isopropanol and gave benzyl 6-azido-2,6-didesoxy-2-[3-nitro-4-(2,3,4,5,6-penta-O-acetyl-D-glucit-1-ylamino)-benzoylamino]-α-D-glucopyranoside, $[\alpha]+30.2°$ (c 0.5; DMSO), MS: m/z 855.6 ([M+Na]$^+$).

D. 2.15 g of triphenylphosphine were added to a solution of 4.16 g of benzyl 6-azido-2,6-didesoxy-2-[3-nitro-4-(2,3,4,5,6-penta-O-acetyl-D-glucit-1-ylamino)-benzoylamino]-α-D-glucopyranoside in 50 ml of tetrahydrofuran and and 1.8 ml of water and the mixture was stirred at room temperature for 20 hours. After concentration, the residue was chromatographed over silica gel with ethyl acetate/methanol and gave benzyl 6-amino-2,6-didesoxy-2-[3-nitro-4-(2,3,4,5,6-penta-O-acetyl-D-glucit-1-ylamino)-benzoylamino]-α-D-glucopyranoside, $[\alpha]+37.4°$ (c 0.5; DMSO), MS: m/z 829.7 ([M+Na]$^+$).

E. 615 mg of 2-chloro-2,4-dimethoxy-1,3,5-triazine were added to a solution of 301 mg of benzene-1,3,5-tricarboxylic acid and 0.35 ml of N-methylmorpholine in ml of absolute dimethylformamide at 0° C. The reaction mixture was stirred at this temperature for 2 hours and then treated with 3.62 g of benzyl-6-amino-2,6-didesoxy-2-[3-nitro-4-(2,3,4,5,6-penta-O-acetyl-D-glucit-1-ylamino)-benzoylamino]-α-D-glucopyranoside. The reaction mixture was stirred at room temperature for 20 hours and then concentrated. The residue was acetylated at room temperature with 40 ml of acetic anhydride in 60 ml of pyridine and, after 5 hours, concentrated. The residue was then taken up in ethyl acetate and extracted with water. The organic phases were washed with dilute sulfuric acid, water and saturated sodium bicarbonate solution, dried over magnesium sulfate and evaporated. The residue was chromatographed over silica gel with methylene chloride/isopropanol and gave benzene-1,3,5-tricarboxylic acid tris-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide], $[\alpha]+65.6°$ (c 0.5; chloroform), MS: m/z 2851.2 ([M+Na]$^+$).

F. A solution of 1.98 g of benzene-1,3,5-tricarboxylic acid tris-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide] in 30 ml of methanol and 20 ml of tetrahydrofuran was treated with 2 ml of a 2% methanolic sodium methanolate solution and stirred at room temperature for 6 hours. The resulting precipitate was filtered off under suction, washed with methanol and dried at 60° C. in a vacuum to give benzene-1,3,5-tricarboxylic acid tris-[[benzyl 2,6-didesoxy-2-(4-D-glucit-1-ylamino-3-nitro-benzoylamino)-α-D-glucopyranosid-6-yl]-amide], $[\alpha]+68.2°$ (c 0.5; dimethyl sulfoxide), MS: m/z 1968.6 ([M+Na]$^+$).

G Sulfation of benzene-1,3,5-tricarboxylic acid tris-[[benzyl 2,6-didesoxy-2-(4-D-glucit-1-ylamino-3-nitro-benzoylamino)-α-D-glucopyranosid-6-yl]-amide] as described in Ex. 29.G. gave benzene-1,3,5-tricarboxylic acid tris-[[benzyl 2,6-didesoxy-2-[4-(2,3,4,5,6-penta-O-sulfα-glucit-1-ylamino)-3-nitro-benzoylamino]-3,4-di-O-sulfo-α-D-glucopyranosid-6-yl]-amide] henicosasodium salt, $[\alpha]+65.0°$ (c 0.5; water), MS: m/z 4085.5 (reconstructed M).

EXAMPLE 31

A. Reaction of (Z)-stilbene-4,4'-dicarboxylic acid with benzyl 6-amino-2,6-didesoxy-2-[3-nitro-4-(2,3,4,5,6-penta-O-acetyl-D-glucit-1-ylamino)-benzoylamino]-α-D-glucopyranoside as described under Ex. 30.E. gave (Z)-stilbene-4,4'-dicarboxylic acid bis-[[benzyl 3,4-di-O-acetyl-2,6-didesoxy-2-[4-(2,3,4,5,6-penta-O- acetyl-D-glucit-1-ylamino)-3-nitro-benzoylamino]-α-D-glucopyranosid-6-yl]-amide], $[\alpha]+74.2°$ (c 0.5; dimethyl sulfoxide), MS: m/z 2036.6 ([M+Na]$^+$).

B. Deacetylation of (Z)-stilbene-4,4'-dicarboxylic acid bis-[[benzyl 3,4-di-O-acetyl-2,6-didesoxy-2-[4-(2,3,4,5,6-penta-O-acetyl-D-glucit- 1-ylamino)-3-nitro-benzoylamino]-α-D-glucopyranosid-6-yl]-amide] as described under Ex. 30.F. gave (Z)-stilbene-4,4'-dicarboxylic acid bis-[[benzyl 2,6-didesoxy-2-(4-D-glucit-1-ylamino-3-nitro-benzoylamino)-α-D-glucopyranosid-6-yl]-amide], $[\alpha]+44.2°$ (c 0.5; dimethyl sulfoxide). C Sulfation of (Z)-stilbene-4,4'-dicarboxylic acid bis-[[benzyl 2,6-didesoxy-2-(4-D-glucit-1-ylamino-3-nitro-benzoylamino)-α-D-glucopyranosid-6-yl]-amide] as described in Ex. 29. G. gave (Z)-stilbene-4,4'-dicarboxylic acid bis-[[benzyl 2,6-didesoxy-2-[4-(2,3,4,5,6-penta-O-sulfα-glucit-1-ylamino)-3-nitro-benzoylamino]-3,4-di-O-sulfo-α-D-glucopyranosid-6-yl] -amide] tetradecasodium salt, $[\alpha]+61.4°$ (c 0.5; water), MS: m/z 2854.5 (reconstructed M).

EXAMPLE 32

A. A solution of 55.0 g of methyl 3-chloro-4-methyl-benzoate (Stempel et al., J. Am. Chem. Soc. 73, 455 (1951)) in 1l of carbon tetrachloride was treated with 53.0 g of N-bromosuccinimide and 100 mg of dibenzoyl peroxide and boiled under reflux for 4 hours while irradiating with a 150 W lamp. The cooled reaction mixture was filtered. The filtrate was concentrated. A solution of the residue in 770 ml of benzene was treated with 83.0 g of triphenylphosphine and heated under reflux for 4 hours. After cooling 380 ml of ether were added. The separated phosphonium salt was filtered off under suction, washed with benzene/ether and dried at 50° C. in a vacuum to give (3-chloro-4-methoxycarbonyl-benzyl)-triphenylphosphonium bromide, MS: m/z 445.4 (M$^+$).

B. A suspension of 52.6 g of (3-chloro-4-methoxycarbonyl-benzyl)-triphenylphosphonium bromide and 16.4 g of methyl 4-formyl-benzoate in 700 ml of tetrahydrofuran was treated dropwise within 30 minutes with 115 ml of a 2% sodium methanolate solution and the mixture was stirred at room temperature for 1 hour. The reaction mixture was suction filtered. The filtrate was concentrated and the residue was chromatographed over silica gel with ethyl acetate/hexane/methylene chloride to give colorless crystals of dimethyl (E)-2-chloro-stilbene-4,4'-dicarboxylate. MS: m/z 330.0 (M$^+$).

C. A suspension of 3.0 g of dimethyl (E)-2-chloro-stilbene-4,4'-dicarboxylate in 30 ml of methanol was treated with 36 ml of 1M sodium hydroxide solution and heated under reflux for 5 hours. After cooling, 37 ml of 1M hydrochloric acid were added dropwise. The resulting slurry was suction filtered; the residue was washed with water and dried at 70° C. in a vacuum to give (E)-2-chloro-stilbene-4,4'-dicarboxylic acid. MS: m/z 302 (M$^+$).

D. Reaction of (E)-2-chloro-stilbene-4,4'-dicarboxylic acid with benzyl 6-amino-2,6-didesoxy-2-[3-nitro-4-(2,3,4,5,6-penta-O-acetyl-D-glucit-1-ylamino)-benzoylamino]-α-D-glucopyranoside as described under Ex. 30.E. gave (E)-2-chloro-stilbene-4,4'-dicarboxylic acid bis-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide]. [α]+54.6° (c 0.5; chloroform). MS: m/z 2071.3 ([M+Na]$^+$).

E. Deacetylation of (E)-2-chloro-stilbene-4,4'-dicarboxylic acid bis-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide] as described under Ex. 30.F. gave (E)-2-chloro-stilbene-4,4'-dicarboxylic acid bis-[[benzyl 2,6-didesoxy-2-(4-D-glucit-1-ylamino-3-nitro-benzoylamino)-α-D-glucopyranosid-6-yl]-amide]. [α]+27.4° (c 0.5; dimethyl sulfoxide). MS: m/z 1481.7 ([M+Na]$^+$).

Sulfation of (E)-2-chloro-stilbene-4,4'-dicarboxylic acid bis-[[benzyl 2,6-didesoxy-2-(4-D-glucit-1-ylamino-3-nitro-benzoylamino)-α-D-glucopyranosid-6-yl]-amide] as described in Ex. 29. G. gave (E)-2-chloro-stilbene-4,4'-dicarboxylic acid bis-[[benzyl 2,6-didesoxy-2-[4-(2,3,4,5,6-penta-O-sulfα-glucit-1-ylamino)-3-nitro-benzoylamino]-3,4-di-O-sulfo-α-D-glucopyranosid-6-yl]-amide] tetradecasodium salt, [a,]+51.6° (c 0.5; water). MS: m/z 2889.5 (reconstructed M).

EXAMPLE 33

A. Reaction of isophthalic acid with benzyl 6-amino-2,6-didesoxy-2-[3-nitro-4-(2,3,4,5,6-penta-O-acetyl-D-glucit-l-ylamino)-benzoylamino]-α-D-glucopyranoside as described under Ex. 30.E. gave isophthalic acid bis-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide]. [α]+68.9° (c 0.5; dimethyl sulfoxide). MS: m/z 1929.8 ([M+Na]$^+$).

B. Deacetylation of isophthalic acid bis-[[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-amide] as described under Ex. 30.F. gave isophthalic acid bis-[[benzyl 2,6-didesoxy-2-(4-D-glucit-1-ylamino-3-nitro-benzoylamino)-α-D-glucopyranosid-6-yl]-amide]. [α]+63.6° (c 0.5; dimethyl sulfoxide). MS: m/z 1345.3 ([M+Na]$^+$).

C. Sulfation of isophthalic acid bis-[[benzyl 2,6-didesoxy-2-(4-D-glucit-1-ylamino-3-nitro-benzoylamino)-α-D-glucopyranosid-6-yl]-amide] as described in Ex. 29. G. gave isophthalic acid bis-[[benzyl 2,6-didesoxy-2-[4-(2,3,4,5,6-penta-O-sulfα-glucit-1-ylamino)-3-nitro-benzoylamino]-3,4-di-O-sulfo-α-D-glucopyranosid-6-yl]-amide] tetradecasodium salt, [α]+75.0° (c 0.5; water). MS: m/z 2751.0 (reconstructed M).

EXAMPLE 34

A. A suspension of 4.8 g of benzyl 6-azido-2-benzyloxycarbonylamino-2,6-didesoxy-α-D-glucopyranoside (see Ex. 9.B.) and 1.35 g of naphthalene-1,4,5,8-tetracarboxylic acid dianhydride in 100 ml of pyridine and 3 ml of triethylamine was heated to 80° C. for 3 hours. Thereafter, 20 ml of acetic anhdride were added dropwise at 70° C. within 15 minutes. After stirring for 1 hour, the reaction mixture was cooled and concentrated. The residue was treated with ice-water and extracted with methylene chloride. The organic phases were washed with dilute sulfuric acid, ice-water, saturated sodium bicarbonate solution and saturated sodium chloride solution, dried over magnesium sulfate and concentrated. The residue was chromatographed over silica gel with methylene chloride/isopropanol. The product fractions were crystallized from methylene chloride ethyl acetate/ether and gave 2,7-bis-(benzyl 3,4-di-O-acetyl-2-benzyloxycarbonylamino-2,6-didesoxy-α-D-glucopyranosid-6-yl)-1,2,3,6,7,8-hexahydro-benzo[lmn][3,8]phenanthroline-1,3,6,8-tetraone. MS: m/z 1222.2 ([M+NH$_4$]$^+$).

B. A solution of 2.89 g of 2,7-bis-(benzyl 3,4-di-O-acetyl-2-benzyloxycarbonylamino-2,6-didesoxy-α-D-glucopyranosid-6-yl)-1,2,3,6,7,8-hexahydro-benzo[lmn][3,8]phenanthroline-1,3,6,8-tetraone in 100 ml of dimethylformamide was hydrogenated at room temperature in the presence of 10% palladium on charcoal for 2 hours. The reaction mixture was suction filtered over a filter aid and the residue was rinsed with ethanol. The filtrates were concentrated to a volume of about 10 ml and used without further purification as crude 2,7-bis-(benzyl 3,4-di-O-acetyl-2-amino-2,6-didesoxy-α-D-glucopyranosid-6-yl)-1,2,3,6,7,8-hexahydro-benzo[lmn][3,8]phenanthroline-1,3,6,8-tetraone in the next step.

C. Reaction of 4-(2,3,4,5,6-penta-O-acetyl-D-glucit-1-ylamino)-3-nitro-benzoic acid (see Ex. 29.C.) with 2,7-bis-(benzyl-3,4-di-O-acetyl-2-amino-2,6-didesoxy-α-D-glucopyranosid-6-yl)-1,2,3,6,7,8-hexahydrobenzo[lmn][3,8]phenanthroline-1,3,6,8-tetraone as described under Ex. 30.E. gave 2,7-bis-[benzyl 3,4-di-O-acetyl-2,6-didesoxy-2-[3-nitro-4-(2,3,4,5,6-penta-O-acetyl-D-glucit-1-ylamino)-benzoylamino]-α-D-glucopyranosid-6-yl]-1,2,3,6,7,8-hexahydro-benzo[lmn][3,8]phenanthroline-1,3,6,8-tetraone. [α]+45.4° (c 0.5; chloroform). MS: m/z 2038.5 ([M+Na]$^+$).

D. Deacetylation of 2,7-bis-[benzyl-3,4-di-O-acetyl-2,6-didesoxy-2-[3-nitro-4-(2,3,4,5,6-penta-O-acetyl-D-glucit 1-ylamino)-benzoylamino]-α-D-glucopyranosid-6-yl]-1,2,3,6,7,8-hexahydro-benzo[lmn][3,8]phenanthroline-1,3,6,8-tetraone as described under Ex. 30.F. gave 2,7-bis-[benzyl 2,6-didesoxy-2-(4-D-glucit- 1-ylamino-3-nitro-benzoylamino)-α-D-glucopyranosid-6-yl]-1,2,3,6,7,8-hexahydro-benzo[lmn][3,8]phenanthroline-1,3,6,8-tetraone. [α]+54.0° (c 0.5; dimethyl sulfoxide). MS: m/z 1447.1 ([M+Na]$^+$).

E. Sulfation of 2,7-bis-[benzyl 2,6-didesoxy-2-(4-D-glucit-1-ylamino-3-nitro-benzoylamino)-α-D-glucopyranosid-6-yl]-1,2,3,6,7,8-hexahydro-benzo[lmn][3,8]phenanthroline-1,3,6,8-tetraone as described in Ex. 29. G. gave 2,7-bis-[benzyl 2,6-didesoxy-2-[3-nitro-4-(2,3,4,5,6-penta-O-sulfα-glucit-1-ylamino)-benzoylamino]-3,4-di-O-sulfo-α-D-glucopyranosid-6-yl]-1,2,3,6,7,8-hexahydro-benzo[lmn][3,8]phenanthroline-1,3,6,8- tetraone tetradecasodium salt. [α]+65.6° (c 0.5; water). MS: m/z 2855.0 (reconstructed M).

EXAMPLE 35

A. 4-Fluoro-3-nitro-benzoic acid was reacted with N-methyl-D-glucamine as described under Example 29.C. and gave 4-[methyl (2,3,4,5,6-penta-O-acetyl-D-glucit-1-yl)-amino]-3-nitro-benzoic acid. [α]+141.2° (c 0.5; chloroform). MS: m/z 593.2 ([M+Na]$^+$).

B. Reaction of 4-[methyl (2,3,4,5,6-penta-O-acetyl-D-glucit-1-yl)-amino]-3-nitro-benzoic acid with benzyl 2-amino-2-desoxy-α-D-glucopyranoside as described under Ex. 30.A. gave benzyl 2-desoxy-2-[4-[methyl (2,3,4,5,6-penta-O-acetyl-D-glucit-1-yl)-amino]-3-nitro-benzoylamino]-α-D-glucopyranoside. [α]+108.8° (c 0.5; chloroform). MS: m/z 822.2 ([M+H]$^+$).

C. Tosylation of benzyl 2-desoxy-2-[4-[methyl (2,3,4,5,6-penta-O-acetyl-D-glucit-1-yl)-amino]-3-nitro-benzoylamino]-α-D-glucopyranoside as described under Ex. 30.B. gave benzyl 2-desoxy-2-[4-[methyl-(2,3,4,5,6-penta-O-acetyl-D-glucit-1-yl)-amino]-3-nitro-benzoylamino]-6-O-(p-tolylsulfonyl)-α-D-glucopyranoside. [α]+78.4° (c 0.5; chloroform). MS: m/z 976.2 ([M+H]$^+$).

D. Reaction of benzyl 2-desoxy-2-[4-[methyl (2,3,4,5,6-penta-O-acetyl-D-glucit-1-yl)-amino]-3-nitro-benzoylamino]-6-O-(p-tolylsulfonyl)-α-D-glucopyranoside as described under Ex. 30.C. gave benzyl 6-azido-2-desoxy-2-[4-[methyl-(2,3,4,5,6-penta-O-acetyl-D-glucit-1-yl)-amino]-3-nitro-benzoylamino]-α-D-glucopyranoside. [α]+64.6° (c 0.5; chloroform). MS: m/z 847.3 ([M+H]$^+$).

E. Reaction of benzyl 6-azido-2-desoxy-2-[4-[methyl (2,3,4,5,6-penta-O-acetyl-D-glucit-1-yl)-amino]-3-nitro-benzoylamino]-α-D-glucopyranoside as described under Ex. 30.D. gave benzyl 6-amino-2-desoxy-2-[4-[methyl (2,3,4,5,6-penta-O-acetyl-D-glucit-1-yl)-amino]-3-nitro-benzoylamino]-α-D-glucopyranoside. [(Y]+137.0° (c 0.5; chloroform). MS: m/z 821.6 ([M+H]$^+$).

F. Reaction of isophthalic acid with benzyl 6-amino-2-desoxy-2-[4-[methyl (2,3,4,5,6-penta-O-acetyl-D-glucit-1-yl)-amino]-3-nitro-benzoylamino]-α-D-glucopyranoside as described under Ex. 30.E. gave isophthalic acid bis-[[benzyl 3,4-di-O-acetyl-2,6-didesoxy-2-[4-[methyl-(2,3,4,5,6-penta-O-acetyl-D-glucit-1-yl)-amino]-3-nitro-benzoylamino]-α-D-glucopyranosid-6-yl]-amide]. [α]+147.4° (c 0.5; chloroform). MS: m/z 1961.5 ([M+Na]$^+$).

G. Deacetylation of isophthalic acid bis-[[benzyl 3,4-di-O-acetyl-2,6-didesoxy-2-[4-[methyl (2,3,4,5,6-penta-O-acetyl-D-glucit-1-yl)-amino]-3-nitro-benzoylamino]-α-D-glucopyranosid-6-yl]-amide] as described under Ex. 30.F. gave isophthalic acid bis-[[benzyl 2,6-didesoxy-2-[4-[(D-glucit-1-yl)-methyl-amino]-3- nitro-benzoylamino]-α-D-glucopyranosid-6-yl]-amide]. [α]+ 148.0° (c 0.5; dimethyl sulfoxide). MS: m/z 1373.1 ([M+Na]$^+$).

H. Sulfation of isophthalic acid bis-[[benzyl 2,6-didesoxy-2-[4-[(D-glucit-1-yl)-methyl-amino]-3-nitro-benzoylamino]-α-D-glucopyranosid-6-yl]-amide] as described in Ex. 29. G. gave isophthalic acid bis-[[benzyl 2,6-didesoxy-2-[4-[methyl (2,3,4,5,6-penta-O-sulfα-glucit-1-yl)-amino]-3-nitro-benzoylamino]-3,4-di-O-sulfo-α-D-glucopyranosid-6-yl]-amide] tetradecasodium salt. [α]+71.0° (c 0.5; water). MS: ml/z 2781.0 (reconstructed M).

EXAMPLE 36

A. 4-Fluoro-3-nitro-benzoic acid was reacted with 1-desoxy-1-(2-hydroxy-ethylamino)-D-glucitol as described under Example 29.C. and gave 4-[(2-acetoxy-ethyl)-(2,3,4,5,6-penta-O-acetyl-D-glucit-1-yl)-amino]-3-nitro-benzoic acid which was processed in crude form in the next step.

B. Reaction of 4-[(2-acetoxy-ethyl)-(2,3,4,5,6-penta-O-acetyl-D-glucit-1-yl)-amino]-3-nitro-benzoic acid as described under Ex. 30.A. gave benzyl-2-[4-[(2-acetoxy-ethyl)-(2,3,4,5,6-penta-O-acetyl-D-glucit-1-yl)-amino]-3-nitro-benzoylamino]-2-desoxy-α-D-glucopyranoside. [α]+103.6° (c 0.5; chloroform). MS: m/z 894.3 ([M+H]$^+$).

C. Tosylation of benzyl 2-[4-[(2-acetoxy-ethyl)-(2,3,4,5,6-penta-O-acetyl-D-glucit-1-yl)-amino]-3-nitro-benzoylamino]-2-desoxy-α-D-glucopyranoside as described under Ex. 30.B. gave benzyl 2-[4-[(2-acetoxy-ethyl)-(2,3,4,5,6-penta-O-acetyl-D-glucit-1-yl)-amino]-3-nitro-benzoylamino]-2-desoxy-6-O-(p-tolylsulfonyl)-α-D-glucopyranoside. [α]+81.4° (c 0.5; chloroform). MS: m/z 1070.9 ([M+Na]$^+$).

D. Reaction of benzyl 2-[4-[(2-acetoxy-ethyl)-(2,3,4,5,6-penta-O-acetyl-D-glucit-1-yl)-amino]-3-nitro-benzoylamino]-2-desoxy-6-O-(p-tolylsulfonyl)-α-D-glucopyranoside as described under Ex. 30.C. gave benzyl 2-[4-[(2-acetoxy-ethyl)-(2,3,4,5,6-penta-O-acetyl-D-glucit-1-yl)-amino]-3-nitro-benzoylamino]-6-azido-2-30 desoxy-α-D-glucopyranoside. [α]+72.8° (c 0.5; chloroform). MS: m/z 919.4 ([M+H]$^+$).

E. Reaction of benzyl 2-[4-[(2-acetoxy-ethyl)-(2,3,4,5,6-penta-O-acetyl-D-glucit-1-yl)-amino]-3-nitro-benzoylamino]-6-azido-2-desoxy-α-D-glucopyranoside as described under Ex. 30.D. gave benzyl 2-[4-[(2-acetoxy-ethyl)-(2,3,4,5,6-penta-O-acetyl-D-glucit-1-yl)-amino]-3-nitro-benzoylamino]-6-amino-2-desoxy-α-D-glucopyranoside. [α]+117.2° (c 0.5; dimethyl sulfoxide). MS: m/z 893.5 ([M+H]$^+$).

F. Reaction of isophthalic acid with benzyl 2-[4-[(2-acetoxyethyl)-(2,3,4,5,6-penta-O-acetyl-D-glucit-1-yl)-amino]-3-nitrobenzoylamino]-6-amino-2-desoxy-α-D-glucopyranoside as described under Ex. 30.E. gave isophthalic acid bis-[[benzyl 2-[4-[(2-acetoxy-ethyl)-(2,3,4,5,6-penta-O-acetyl-D-glucit-1-yl)-amino]-3-nitro-benzoylamino]-3,4-di-O-acetyl-2,6-didesoxy-(α-D-glucopyranosid-6-yl]-amide]. [α]+135.0° (c 0.5; chloroform). MS: m/z 2105.6 ([M+Na]$^+$).

G. Deacetylation of isophthalic acid bis-[[benzyl 2-[4-[(2-acetoxy-ethyl)-(2,3,4,5,6-penta-O-acetyl-D-glucit-1-yl)-amino]-3-nitro-benzoylamino]-3,4-di-O-acetyl-2,6-didesoxy-α-D-glucopyranosid-6-yl]-amide] as described under Ex. 30.F. gave isophthalic acid bis-[[benzyl 2,6-didesoxy-2-[4-[(D-glucit-1-yl)-(2-hydroxy-ethyl)-amino]-3-nitro-benzoylamino]-α-D-glucopyranosid-6-yl]-amide]. [α]+96.4° (c 0.5; dimethyl sulfoxide). MS: m/z 1433.3 ([M+Na]$^+$).

H. Sulfation of isophthalic acid bis-[[benzyl 2,6-didesoxy-2-[4-[(D-glucit-1-yl)-(2-hydroxy-ethyl)-amino]-3-nitro-benzoyl-amino]-α-D-glucopyranosid-6-yl]-amide] as described in Ex. 29. G. gave isophthalic acid bis-[[benzyl 2,6-didesoxy-2-[4-[(2-hydroxy-sulfonyloxy-ethyl)-2,3,4,5,6-penta-O-sulfα-glucit-1-yl)-amino]-3-nitro-benzoylamino]-3,4-di-O-sulfo-α-D-glucopyranosid-6-yl]-amide] hexadecasodium salt. [α]+73.2° (c 0.5; water). MS: m/z 3045.0 (reconstructed M).

EXAMPLE 37

A. A solution of 17.1 g of 4-[methyl (2,3,4,5,6-penta-O-acetyl-D-glucit-1-yl)-amino]-3-nitro-benzoic acid (see Ex. 35.A.) in 515 ml of ethanol was hydrogenated at room temperature in the presence of 10% palladium on active charcoal for 3 hours. The reaction mixture was suction filtered over a filter aid and the residue was washed with ethanol. The filtrate was concentrated and the residue was acetylated at room temperature with 250 ml of acetic anhydride in 500 ml of pyridine for 16 hours. After concentration in a vacuum, the residue was stirred for 2 hours in 150 ml of tetrahydrofuran, 60 ml of water and 10 ml of pyridine. The reaction mixture was again concentrated. The residue was treated with ice-water and acidified (pH 3) with 2N hydrochloric acid. The solution was extracted twice with ethyl acetate. The organic phase was washed with ice-water and saturated sodium chloride solution, dried over magnesium sulfate and concentrated. The residue was chromatographed over silica gel with methylene chloride/isopropanol and gave 3-acetylamino-4-[methyl (2,3,4,5,6-penta-O-acetyl-D-glucit-1-yl)-amino]-benzoic acid, [α]+3.4° (c 0.5; chloroform), MS: m/z 581.3 ([M+H]$^+$).

B. Reaction of 3-acetylamino-4-[methyl (2,3,4,5,6-penta-O-acetyl-D-glucit-1-yl)-amino]-benzoic acid with benzyl 2-amino-2-desoxy-α-D-glucopyranoside as described under Ex. 30.A. gave benzyl 2-[3-acetylamino-4-[methyl (2,3,4,5,6-penta-O-acetyl-D-glucit-1-yl)-amino]-benzoylamino]-2-desoxy-α-D-glucopyranoside, [α]+48.8° (c 0.5; dimethyl sulfoxide), MS: m/z 834.4 ([M+H]$^+$).

C. Tosylation of benzyl 2-[3-acetylamino-4-[methyl 2,3,4,5,6-penta-O-acetyl-D-glucit-1-yl)-amino]-benzoylamino]-2-desoxy-α-D-glucopyranoside as described under Ex. 30.B. gave benzyl-2-[3-acetylamino-4-[methyl-(2,3,4,5,6-penta-O-acetyl-D-glucit-1-yl)-amino]-benzoylamino]-2-desoxy-6-O-(p-tolylsulfonyl)-α-D-glucopyranoside, [α]+44.4° (c 0.5; dimethyl sulfoxide), MS: m/z 1010.6 ([M+Na]$^+$).

D. Reaction of benzyl 2-[3-acetylamino-4-[methyl (2,3,4,5,6-penta-O-acetyl-D-glucit-1-yl)-amino]-benzoylamino]-2-desoxy-6-O-(p-tolylsulfonyl)-α-D-glucopyranoside as described under Ex. 30.C. gave benzyl 2-[3-acetylamino-4-[methyl (2,3,4,5,6-penta-O-acetyl-D-glucit-1-yl)-amino]-benzoylamino]-6-azido-2,6-didesoxy-α-D-glucopyranoside, [α]+44.0° (c 0.5; dimethyl sulfoxide), MS: m/z 881.5 ([M+Na]$^+$).

E. Reaction of benzyl 2-[3-acetylamino-4-[methyl (2,3,4,5,6-penta-O-acetyl-D-glucit-1-yl)-amino]-benzoylamino]-6-azido-2,6-didesoxy-α-D-glucopyranoside as described under Ex. 30.D. gave benzyl 2-[3-acetylamino-4-[methyl (2,3,4,5,6-penta-O-acetyl-D-glucit-1-yl)-amino]-benzoylamino]-6-amino-2,6-didesoxy-α-D-glucopyranoside-α-D-glucopyranoside, [α]+58.6° (c 0.5; methanol), MS: m/z 833.5 ([M+H]+).

F. Reaction of isophthalic acid with benzyl 2-[3-acetylamino-4-[methyl (2,3,4,5,6-penta-O-acetyl-D-glucit-1-yl)-amino]-benzoylamino]-6-amino-2,6-didesoxy-α-D-glucopyranoside-α-D-glucopyranose as described under Ex. 30.E. gave isophthalic acid bis-[[benzyl 3,4-di-O-acetyl-2-[3-acetylamino-4-[methyl (2,3,4,5,6-penta-O-acetyl-D-glucit-1-yl)-amino]-benzoylamino]-2,6-didesoxy-α-D-glucopyranosid-6-yl]-amide], [α]+70.0° (c 0.5; chloroform), MS: m/z 1985.6 ([M+Na]$^+$).

G. Deacetylation of isophthalic acid bis-[[benzyl 3,4-di-O-acetyl-2-[3-acetylamino-4-[methyl-(2,3,4,5,6-penta-O-acetyl-D-glucit-1-yl)-amino]-benzoylamino]-2,6-didesoxy-α-D-glucopyranosid-6-yl]-amide] as described under Ex. 30.F. gave isophthalic acid bis-[[benzyl 2-[3-acetylamino-4-[D-glucit-1-yl)-methylamino]-benzoylamino]-2,6-didesoxy-α-D-glucopyranosid-6-yl]-amide], [α]+128.8° (c 0.5; dimethyl sulfoxide), MS: m/z 1397.2 ([M+Na]$^+$).

H. Sulfation of isophthalic acid bis-[[benzyl 2-[3-acetylamino-4-[D-glucit-1-yl)-methylamino]-benzoylamino]-2,6-didesoxy-α-D-glucopyranosid-6-yl]-amide] as described in Ex. 29. G. gave isophthalic acid bis-[[benzyl 2-[3-acetylamino-4-[methyl-(2,3,4,5,6-penta-O-sulfα-glucit-1-yl)-amino]-benzoylamino]-2,6-didesoxy-3,4-di-O-sulfo-α-D-glucopyranosid-6-yl]-amide] tetradecasodium salt, [α]+47.0° (c 0.5; water), MS: m/z 2804.0 (reconstructed M).

EXAMPLE 38

A. Reaction of 4-[(2-acetoxy-ethyl)-(2,3,4,5,6-penta-O-acetyl-D-glucit-1-yl)-amino]-3-nitro-benzoic acid (see Ex. 36.A.) as described under Ex. 37.A. gave 4-[(2-acetoxy-ethyl)-(2,3,4,5,6-penta-O-acetyl-D-glucit-1-yl)-amino]-3-acetylamino-benzoic acid which was used in the crude state in the next step.

B. Reaction of 4-[(2-acetoxy-ethyl)-(2,3,4,5,6-penta-O-acetyl-D-glucit-1-yl)-amino]-3-acetylamino-benzoic acid with benzyl-2-amino-2-desoxy-α-D-glucopyranoside as described under Ex. 30.A. gave benzyl-2-[4-[(2-acetoxy-ethyl)-(2,3,4,5,6-penta-O-acetyl-D-glucit-1-yl)-amino]-3-acetylamino-benzoylamino]-2-desoxy-α-D-glucopyranoside, [a:]+32.8° (c 0.5; dimethyl sulfoxide), MS: m/z 906.5 ([M+H]$^+$).

C. Tosylation of benzyl-2-[4-[(2-acetoxy-ethyl)-(2,3,4,5,6-penta-O-acetyl-D-glucit-1-yl)-amino]-3-acetylamino-benzoyl-amino]-2-desoxy-α-D-glucopyranoside as described under Ex. 30.B. gave benzyl-2-[4-[(2-acetoxy-ethyl)-(2,3,4,5,6-penta-O-acetyl-D-glucit-1-yl)-amino]-3-acetylamino-benzoylamino]-2-desoxy-6-O-(p-tolylsulfonyl)-α-D-glucopyranoside, [α]+27.2° (c 0.5; dimethyl sulfoxide), MS: m/z 1082.5 ([M+Na]$^+$).

D. Reaction of benzyl 2-[4-[(2-acetoxy-ethyl)-(2,3,4,5,6-penta-O-acetyl-D-glucit-1-yl)-amino]-3-acetylamino-benzoylamino]-2-desoxy-6-O-(p-tolylsulfonyl)-α-D-glucopyranoside as described under Ex. 30.C. gave benzyl 2-[4-[(2-acetoxy-ethyl)-(2,3,4,5,6-penta-O-acetyl-D-glucit-1-yl)-amino]-3-acetylamino-benzoyl-amino]-6-azido-2,6-didesoxy-α-D-glucopyranoside, [α]+24.6° (c 0.5; dimethyl sulfoxide), MS: m/z 953.6 ([M+Na]$^+$).

E. Reaction of benzyl 2-[4-[(2-acetoxy-ethyl)-(2,3,4,5,6-penta-O-acetyl-D-glucit-1-yl)-amino]-3-acetylamino-benzoylamino]-6-azido-2,6-didesoxy-α-D-glucopyranoside as described under Ex. 30.D. gave benzyl 2-[4-[(2-acetoxy-ethyl)-(2,3,4,5,6-penta-O-acetyl-D-glucit-1-yl)-amino]-3-acetylamino-benzoylamino]-6-amino- 2,6-didesoxy-α-D-glucopyranoside, [α]+42.8° (c 0.5; methanol), MS: m/z 905.6 ([M+H]$^+$).

F. Reaction of isophthalic acid with benzyl 2-[4-[(2-acetoxy-ethyl)-(2,3,4,5,6-penta-O-acetyl-D-glucit-1-yl)-amino]-3-acetylamino-benzoylamino]-6-amino-2,6-didesoxy-α-D-glucopyranoside as described under Ex. 30.E. gave isophthalic acid bis-[[benzyl 2-[4-[(2-acetoxy-ethyl)-(2,3,4,5,6-penta-O-acetyl-D-glucit-1-yl)-amino]-3-acetylamino-benzoylamino]-3,4-di-O-acetyl-2,6-didesoxy-α-D-glucopyranosid-6-yl]-amide], [α]+43.6° (c 0.4; chloroform), MS: m/z 2129.3 ([M+Na]$^+$).

G. Deacetylation of isophthalic acid bis-[[benzyl 2-[4-[(2-acetoxy-ethyl)-(2,3,4,5,6-penta-O-acetyl-D-glucit-1-yl)-amino]-3-acetylamino-benzoylamino]-3,4-di-O-acetyl-2,6-didesoxy-α-D-glucopyranosid-6-yl]-amide] as described under Ex. 30.F. gave isophthalic acid bis-[[benzyl 2-[3-acetylamino-4-[D-glucit-1-yl-(2-hydroxy-ethyl)-amino]-benzoylamino]-2,6-didesoxy-α-D- glucopyranosid-6-yl]-amide], [α]+88.4° (c 0.5; dimethyl sulfoxide). MS: m/z 1457.6 ([M+Na]⁺).

H. Sulfation of isophthalic acid bis-[[benzyl 2-[3-acetylamino-4-[D-glucit-1-yl-(2-hydroxy-ethyl)-amino]-benzoylamino]-2,6-didesoxy-α-D-glucopyranosid-6-yl]-amide] as described in Ex. 29.G. gave isophthalic acid bis-[[benzyl 2-[3-acetylamino-4-[(2,3,4,5,6-penta-O-sulfα-glucit-1-yl)-(2-sulfonyloxy-ethyl)-amino]-benzoylamino]-2,6-didesoxy-3,4-di-O-sulfo-α-D-glucopyranosid-6-yl]-amide] hexadecasodium salt, [α]+48.8° (c 0.5; water). MS: m/z 3068.2 (reconstructed M).

EXAMPLE 39

A. Reaction of monomethyl isophthalate with benzyl 6-amino-2-benzyloxycarbonylamino-2,6-didesoxy-u-D-glucopyranoside (see Ex. 9.C.) as described under Ex. 30.A. gave methyl N-(benzyl 2-benzyloxycarbonylamino-2,6-didesoxy-o.-D-glucopyranosid-6-yl)-isophthalamate, [α]+81.4° (c 0.5; dimethyl sulfoxide). MS: m/z 565.7 ([M+H]+).

B. A solution of 3.8 g of methyl N-(benzyl 2-benzyloxycarbonylamino-2,6-didesoxy-α-D-glucopyranosid-6-yl)-isophthalamate in 80 ml of methanol was treated with 6.6 ml of 2M sodium hydroxide solution, heated under reflux for 2.5 hours and then concentrated. The residue was taken up in 200 ml of warm water and acidified with 10 ml of 2N hydrochloric acid. The colorless precipitate was filtered off under suction, rinsed with water and dried at 70° C. in a drying oven to give N-(benzyl 2-benzyloxycarbonylamino-2,6-didesoxy-α-D-glucopyranosid-6-yl)-isophthalamic acid, [α]+87.6° (c 0.5; dimethyl sulfoxide). MS: m/z 549.5 ([M−H]⁻).

C. N-(benzyl 2-benzyloxycarbonylamino-2,6-didesoxy-α-D-glucopyranosid-6-yl)-isophthalamic acid was reacted with 2,3,4,5,6-penta-O-acetyl-D-gluconic acid (benzyl 3,4-di-O-acetyl-2-amino-2,6-didesoxy-α-D-glucopyranosid-6-yl)-amide (see Ex. 14.C.) as described under Ex. 30.A. Subsequent acetylation as described e.g. under Ex. 14.B. gave N-(benzyl 3,4-di-O-acetyl-2-benzyloxycarbonylamino-2,6-didesoxy-α-D-glucopyranosid-6-yl)-N'-[(benzyl 3,4-di-O-acetyl-2,6-didesoxy-6-(2,3,4,5,6-penta-O-acetyl-D-gluconylamino)-α-D-glucopyranosid-2-yl]-isophthalamide, [α]+93.0° (c 0.5; chloroform). MS: m/z 1379.3 ([M+Na]⁺).

D. Hydrogenation of N-(benzyl 3,4-di-O-acetyl-2-benzyloxy-carbonylamino-2,6-didesoxy-α-D-glucopyranosid-6-yl)-N'-[(benzyl 3,4-di-O-acetyl-2,6-didesoxy-6-(2,3,4,5,6-penta-O-acetyl-D-gluconylamino)-α-D-glucopyranosid-2-yl]-isophthal-amide as described under Ex. 13.B. gave N-(benzyl 3,4-di-O-acetyl-2-amino-2,6-didesoxy-α-D-glucopyranosid-6-yl)-N'-[(benzyl 3,4-di-O-acetyl-2,6-didesoxy-6-(2,3,4,5,6-penta-O-acetyl-D-gluconylamino)-α-D-glucopyranosid-2-yl]-isophthalamide, [α]+87.6° (c 0.25; dimethyl sulfoxide). MS: m/z 1246.9 ([M+Na]⁺).

E. Reaction of 4-(2,3,4,5,6-penta-O-acetyl-D-glucit-1-ylamino)-3-nitro-benzoic acid (see Ex. 29.C.) with N-(benzyl 3,4-di-O-acetyl- 2-amino-2,6-didesoxy-α-D-glucopyranosid-6-yl)-N'-[(benzyl 3,4-di-O-acetyl-2,6-didesoxy-6-(2,3,4,5,6-penta-O-acetyl-D-gluconylamino)-α-D-glucopyranosid-2-yl]-isophthalamide as described under Ex. 30.A. gave N-[benzyl 3,4-di-O-acetyl-2,6-didesoxy-2-[4-(2,3,4,5,6-penta-O-acetyl-D-glucit-1-ylamino)-3-nitro-benzoylamino]-α-D-glucopyranosid-6-yl]-N'-[(benzyl 3,4-di-O-acetyl-2,6-didesoxy-6-(2,3,4,5, 6-penta-O-acetyl-D-gluconylamino)-α-D-glucopyranosid-2-yl]-isophthalamide, [α]+81.4° (c 0.5; dimethyl sulfoxide). MS: m/z 565.7 ([M+H]⁺).

F. Deacetylation of N-[benzyl 3,4-di-O-acetyl-2,6-didesoxy-2-[4-(2,3 ,4,5 ,6-penta-O-acetyl-D-glucit-1-ylamino)-3-nitro-benzoylamino]-α-D-glucopyranosid-6-yl]-N'-[(benzyl 3,4-di-O-acetyl-2,6-didesoxy-6-(2,3,4,5,6-penta-O-acetyl-D-gluconyl-amino)-α-D-glucopyranosid-2-yl]-isophthalamide as described under Ex. 30.F. gave N-[benzyl 2,6-didesoxy-2-(4-D-glucit-1-ylamino)-3-nitro-benzoylamino)-α-D-glucopyranosid-6-yl]-N'-(benzyl 2,6-didesoxy-6-D-gluconylamino-α-D-glucopyranosid-2-yl)-isophthalamide, [α]+86.8° (c 0.5; dimethyl sulfoxide). MS: m/z 1195.9 ([M+Na]⁺).

G. Sulfation of N-[benzyl 2,6-didesoxy-2-(4-D-glucit-1-yl-amino)-3-nitro-benzoylamino)-α-D-glucopyranosid-6-yl]-N'-(benzyl 2,6-didesoxy-6-D-gluconylamino-α-D-glucopyranosid-2-yl)-isophthalamide as described in in Ex. 29.G. gave N-[benzyl 2,6-didesoxy-2-[4-(2,3,4,5,6-penta-O-sulfα-glucit-1-ylamino)-3-nitro-benzoylamino]-3,4-di-O-sulfo-α-D-glucopyranosid-6-yl]-N'-[(benzyl 2,6-didesoxy-6-(2,3,4,5,6-penta-O-sulf-D-gluconylamino)-3,4-di-O-sulfo-α-D-glucopyranosid-2-yl]-isophthalamide tetradecasodium salt, [α]+48.8° (c 0.5; water). MS: m/z 3068.2 (reconstructed M).

Example A

Tablets:

| | | |
|---|---|---|
| 1 | Compound of formula Ia-Ic | 500 mg |
| 2 | Lactose, anhydrous | 150 mg |
| 3 | Microcrystalline cellulose | 150 mg |
| 4 | Polyvinylpyrrolidone | 40 mg |
| 5 | Talc | 50 mg |
| 6 | Magnesium stearate | 10 mg |
| | Tablet weight | 900 mg |

Ingredients 1–4 are sieved and mixed. This mixture is granulated with demineralized water and the dried granulate is mixed with ingredients 5 and 6. The resulting mixture is pressed to tablets of suitable form.

Example B

Pellets:

| | | |
|---|---|---|
| 1 | Compound of formula Ia-Ic | 500 mg |
| 2 | Microcrysalline cellulose | 200 mg |
| 3 | PRIMOJEL | 70 mg |
| 4 | Flavor powder | 10 mg |
| 5 | Talc | 20 mg |

The mixed and sieved ingredients 1–3 are moistened sufficiently with demineralized water and pressed through a suitable perforated disc using an extruder. The extrudate is transferred to a pelleting plate, rounded-off to beadlets and subsequently dried. The dried beadlets are treated with sieved ingredients 4 and 5 and filled into paper sachets or similar dosage form.

Example C

Injection solution:

In order to produce an injection solution, 50 mg of compound of formula Ia–Ic and 0.5 mg of Tris buffer are dissolved in water for injection ad 1 ml and the pH is adjusted to 7.4. The solution is filtered sterile and, after filling into ampules, autoclaved.

We claim:
1. A compound of formula:

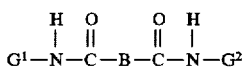   Ia or

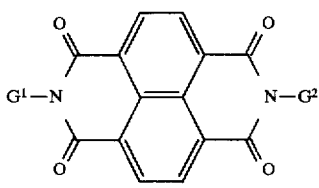   Ib wherein,

B is lower alkylene, an unsubstituted aromatic ring system or a substituted aromatic ring system;

$G^1$ and $G^2$ each independently are:

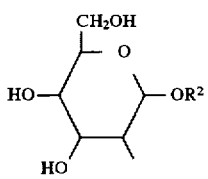   a)

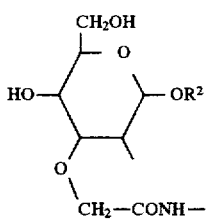   b)

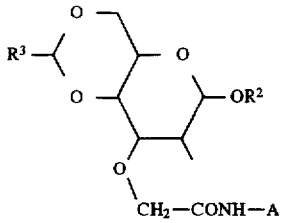   c)

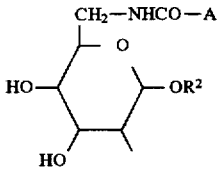   d)

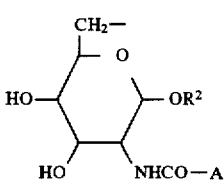   e)

or

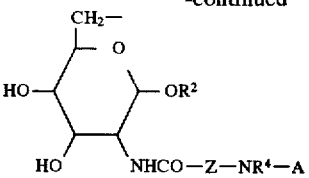   f)

in which in each case at least one hydroxy group of a)–f) is esterified with sulfuric acid and wherein $R^2$ is hydrogen, lower alkyl or benzyl;
$R^3$ is hydrogen, lower alkyl or phenyl;
$R^4$ is hydrogen, unsubstituted lower alkyl or substituted lower alkyl;
Z is unsubstituted phenylene or substituted phenylene;
A is a sugar alcohol devoid of the 1-hydroxy group, a mono-deoxygenated sugar alcohol, a multiply-deoxygenated sugar alcohol, glycopyranoside, tris-(hydroxymethyl)-methyl, glycopyranose, or a residue of formula:

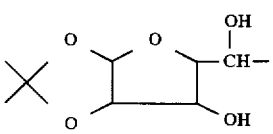   g)

or

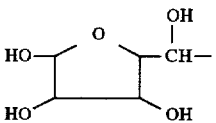   h)

in which in each case at least one hydroxy group in A is esterified with sulfuric acid;

or pharmaceutically acceptable salts thereof.

2. The compound in accordance with claim 1, wherein $G^1$ and $G^2$ are the same.

3. The compound in accordance with claim 1, wherein B is phenylene, naphthylene or a group of the formula:

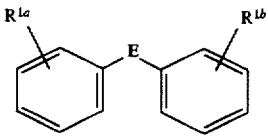

wherein

E is a carbon-carbon bond, —O—, —CO, —CH$_2$—, —CH$_2$CH$_2$—, —CH=CH— or —C≡C— and $R^{1a}$ and $R^{1b}$ are hydrogen or halogen.

4. The compound in accordance with claim 2, wherein B is phenylene, naphthylene or a group of the formula:

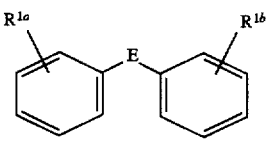

wherein

E is a carbon-carbon bond, —O—, —CO, —CH$_2$—, —CH$_2$CH$_2$—, —CH=CH— or —C≡C— and $R^{1a}$ and $R^{1b}$ are hydrogen or halogen.

5. The compound in accordance with claim 1, wherein the sugar alcohol of A is glucitol, galactitol, mannitol, gulitol, arabinitol, ribitol, xylitol, threitol, erythritol, or glycerol.

6. The compound in accordance with claim 5, wherein $R^2$ is benzyl.

7. The compound of claim 1 which is (Biphenyl-4,4'-dicarboxylic acid)-bis-[[benzyl 3-O-[(benzyl 2-desoxy-2,3,4-tri-O-sulfo-α-D-glucopyranosid)-2-ylcarbamoylmethyl]-4,6-(R)-O-benzylidene-2-desoxy-α-D-glucopyranosid-2-yl]-amide].

8. The compound of claim 1 which is biphenyl-4,4'-dicarboxylic acid bis-[[benzyl 2,6-didesoxy-3,4-di-O-sulfo-6-(2,3,4,5,6-penta-O-sulf-D-gluconoylamino)-α-D-glucopyranosid-2-yl]-amide].

9. The compound of claim 1 which is biphenyl-4,4'-dicarboxylic acid bis-[[(Z)-benzyl 2,6-didesoxy-3,4-di-O-sulfo-6-(3-desoxy-2,4,5,6-tetra-O-sulf-D-erythro-hex-2-enonoylamino)-α-D-glucopyranosid-2-yl]-amide].

10. The compound of claim 1 which is (Z)-stilbene-4,4'-dicarboxylic acid bis-[[benzyl 2,6-didesoxy-6-(2,3,4,5,6-penta-O-sulf-D-gluconoylamino)-3,4-di-O-sulfo-oα-D-glucopyranosid-2-yl]-amide].

11. The compound of claim 1 which is isophthalic acid bis-[[benzyl 2,6-didesoxy-6-(2,3,4,5,6-penti-O-sulf-D-gluconoylamino)-3,4-di-O-sulfo-α-D-glucopyranosid-2-yl]-amide].

12. The compound of claim 1 which is benzene-1,3,5-tricarboxylic acid tris-[[benzyl 2,6-didesoxy-2-[4-(2,3,4,5,6-penta-O-sulf-D-glucit-1-ylamino)-3-nitro-benzoylamino]-3,4-di-O-sulfo-α-D-glucopyranosid-6-yl]-amide].

13. The compound of claim 1 which is (E)-2-chlorostilbene-4,4'-dicarboxylic acid bis-[[benzyl 2,6-didesoxy-2-[4-(2,3,4,5,6-penta-O-sulf-D-glucit-1-ylamino)-3-nitro-benzoylamino]-3,4-di-O-sulfo-α-D-glucopyranosid-6-yl]-amide].

14. The compound of claim 1 which is isophthalic acid bis-[[benzyl 2,6-didesoxy-2-[4-(2,3,4,5,6-penta-O-sulf-D-glucit-1-ylamino)-3-nitro-benzoylamino]-3,4-di-O-sulfo-α-D-glucopyranosid-6-yl]-amide].

15. The compound of claim 1 which is 2,7-bis-[benzyl 2,6-didesoxy-2-[3-nitro-4-(2,3,4,5,6-penta-O-sulf-D-glucit-1-ylamino)-benzoylamino]-3,4 Idi-O-sulfo-α-D-glucopyranosid-6-yl]-1,2,3,6,7,8-hexahydro-benzo[lmn][3,8]phenanthroline-1,3,6,8-tetraone.

16. The compound of claim 1 which is isophthalic acid bis-[[benzyl 2,6-didesoxy-2-[4-[methyl (2,3,4,5,6-penta-O-sulf-D-glucit-1-yl)-amino]-3-nitro-benzoylamino]-3,4-di-O-sulfo-α-D-glucopyranosid-6-yl]-amide].

17. The compound of claim 1 which is isophthalic acid bis-[[benzyl 2,6-didesoxy-2-[4-[(2-hydroxy-sulfonyloxy-ethyl)-2,3,4,5,6-penta-O-sulf-D-glucit-1-yl)-amino]-3-nitro-benzoylamino]-3,4-di-O-sulfo-α-D-glucopyranosid-6-yl]-amide].

18. The compound of claim 1 which is isophthalic acid bis-[[ benzyl 2-[3-acetylamino-4-[methyl-(2,3,4,5,6-penta-O-sulf-D-glucit-1-yl)-amino]-benzoylamino]-2,6-didesoxy-3,4-di-O-sulfo-α-D-glucopyranosid-6-yl]-amide].

19. The compound of claim 1 which is isophthalic acid bis-[[benzyl 2-[3-acetylamino-4-[(2,3,4,5,6-penta-O-sulf-D-glucit-1-yl)-(2-sulfonyloxy-ethyl)-amino]-benzoylamino]-2,6-didesoxy-3,4-di-O-sulfo-α-D-glucopyranosid-6-yl]-amide].

\* \* \* \* \*

UNITED STATES PATENT AND TRADEMARK OFFICE
CERTIFICATE OF CORRECTION

| | | |
|---|---|---|
| PATENT NO. : | 5,767,268 | Page 1 of 2 |
| DATED : | June 16, 1998 | |
| INVENTOR(S) : | Chucholowski et al. | |

It is certified that error appears in the above-identified patent and that said Letters Patent is hereby corrected as shown below:

Column 49, claim 10, line 18, "penta-O-sulf-D-" should be -- penta-O-sulfo-D- --
line 18, "-sulfo-oα-D-" should be -- -sulfo-α-D- --

Column 49, claim 11, line 21, "-penti-O-sulf-D-" should be --penta-O-sulfo-D- --

Column 49, claim 12, line 25, "-O-sulf-D-" should be -- -O-sulfo-D- --

Column 49, claim 13, line 29, "-O-sulf-D-" should be -- -O-sulfo-D- --

Column 50, claim 14, line 2, "-O-sulf-D-" should be -- -O-sulfo-D- --

Column 50, claim 15, line 6, "-O-sulf-D-" should be -- -O-sulfo-D- --
line 7, "-3,4 Idi-O-" should be ---3,4-di-O- --

Column 50, claim 16, line 12, "sulf-D-" should be -- sulfo-D- --

UNITED STATES PATENT AND TRADEMARK OFFICE
CERTIFICATE OF CORRECTION

PATENT NO. : 5,767,268
DATED : June 16, 1998
INVENTOR(S) : Chucholowski et al.

It is certified that error appears in the above-identified patent and that said Letters Patent is hereby corrected as shown below:

Column 50, claim 17, line 16, "-penta-O-sulf-D-" should be -- -penta-O-sulfo-D- --

Column 50, claim 18, line 21, "-O-sulf-D-" should be -- -O-sulfo-D- --

Column 50, claim 19, line 24, "-penta-O-sulf-D-" should be -- -penta-O-sulfo-D- --

Signed and Sealed this

Twenty-second Day of September, 1998

Attest:

BRUCE LEHMAN

Attesting Officer

Commissioner of Patents and Trademarks